US009623257B2

(12) United States Patent
Olson et al.

(10) Patent No.: US 9,623,257 B2
(45) Date of Patent: Apr. 18, 2017

(54) RECHARGE TUNING TECHNIQUES FOR AN IMPLANTABLE DEVICE

(75) Inventors: David P. Olson, Minnetrista, MN (US); Nicholas A. Delisi, Blaine, MN (US); Jay T. Eisch, Wyoming, MN (US); Philip R. LaBrosse, Arden Hills, MN (US); Joseph J. Nolan, Minnetonka, MN (US)

(73) Assignee: Medtronic, Inc., Minneapolis, MN (US)

( * ) Notice: Subject to any disclaimer, the term of this patent is extended or adjusted under 35 U.S.C. 154(b) by 1384 days.

(21) Appl. No.: 13/439,591

(22) Filed: Apr. 4, 2012

(65) Prior Publication Data
US 2012/0262108 A1 Oct. 18, 2012

Related U.S. Application Data

(60) Provisional application No. 61/476,584, filed on Apr. 18, 2011.

(51) Int. Cl.
*H02J 7/00* (2006.01)
*A61N 1/378* (2006.01)
*H02J 7/02* (2016.01)

(52) U.S. Cl.
CPC ............ *A61N 1/3787* (2013.01); *H02J 7/025* (2013.01)

(58) Field of Classification Search
CPC .............................. A61N 1/3787; H02J 7/025
USPC ............................................ 30/108; 320/108
See application file for complete search history.

(56) References Cited

U.S. PATENT DOCUMENTS

| 5,690,693 A | * | 11/1997 | Wang | A61N 1/3787 607/61 |
| 5,713,939 A | | 2/1998 | Nedungadi et al. | |
| 5,995,874 A | * | 11/1999 | Borza | A61N 1/3787 607/61 |
| 6,850,803 B1 | * | 2/2005 | Jimenez | A61N 1/3787 607/33 |
| 7,515,967 B2 | | 4/2009 | Phillips et al. | |

(Continued)

FOREIGN PATENT DOCUMENTS

EP  1731097 A2  12/2006

OTHER PUBLICATIONS

International Search Report and The Written Opinion of the International Searching Authority, mailed Jan. 2, 2013, from co-pending PCT Application, PCT/US2012/032468.

*Primary Examiner* — Richard V Muralidar
(74) *Attorney, Agent, or Firm* — Beth L. McMahon; Medtronic, Inc.

(57) ABSTRACT

Techniques are disclosed for tuning a frequency at which an external device transcutaneously transfers energy. The transferred energy may be used to charge a rechargeable power source of an implantable medical device (IMD) and/or to power the IMD directly. One embodiment relates to a charging system that may comprise a circuit to drive a primary coil of an external device at a drive frequency and a control circuit to tune the drive frequency based on a characteristic of a monitored signal that is associated with the primary coil. The characteristic is not present when the primary coil is being driven at a resonant frequency of the system. In a specific example, the characteristic comprises a stub pulse and the control circuit is configured to tune the drive frequency based on at least one of a relative timing and a width of the stub pulse.

32 Claims, 14 Drawing Sheets

(56) References Cited

U.S. PATENT DOCUMENTS

| | | | |
|---|---|---|---|
| 7,650,192 B2 | 1/2010 | Wahlstrand | |
| 7,780,613 B2 | 8/2010 | Sherman | |
| 8,005,547 B2 | 8/2011 | Forsberg et al. | |
| 8,024,047 B2 | 9/2011 | Olson et al. | |
| 8,912,686 B2* | 12/2014 | Stoner, Jr. | H02J 5/005 307/104 |
| 2005/0119716 A1 | 6/2005 | McClure et al. | |
| 2008/0239762 A1* | 10/2008 | Jacques | H02M 3/33538 363/21.02 |
| 2009/0174263 A1* | 7/2009 | Baarman | H02J 5/005 307/104 |
| 2010/0106223 A1 | 4/2010 | Grevious et al. | |
| 2010/0106233 A1 | 4/2010 | Grant et al. | |
| 2011/0057606 A1 | 3/2011 | Saunamaki | |

\* cited by examiner

RECHARGE TUNING TECHNIQUES FOR AN IMPLANTABLE DEVICE

RELATED APPLICATIONS

This application claims priority to provisionally-filed patent application having Ser. No. 61/476,584 filed on Apr. 18, 2011 entitled "RECHARGE TUNING TECHNIQUES FOR AN IMPLANTABLE DEVICE", which is incorporated herein by reference in its entirety.

BACKGROUND

Implantable medical devices for producing a therapeutic result in a patient are well known. Examples of such implantable medical devices include drug infusion pumps, implantable neurostimulators, cardioverters, cardiac pacemakers, defibrillators and cochlear implants. Of course, it is recognized that other implantable medical devices are envisioned which utilize energy delivered or transferred from an external device.

A common element in all of these implantable medical devices is the need for electrical power in the implanted medical device. The implanted medical device requires electrical power to perform its therapeutic function, which may include driving an electrical infusion pump, providing an electrical neurostimulation pulse or providing an electrical cardiac stimulation pulse. This electrical power is derived from a power source.

Some implantable medical devices can receive electrical power transcutaneously through the use of inductive coupling. For instance, power can be transferred by inductively coupling an external primary coil that is positioned on or near the skin of a patient with a secondary coil that is coupled to, or included within, an implantable medical device. Current induced in the secondary coil may be used to store energy in a power source such as a rechargeable battery and/or could be used to directly power circuitry within the implantable device. Once recharged, the internal power source may be used to supply electrical power to the implanted medical device.

Many devices and techniques have been developed to provide transcutaneous energy to power an implantable medical device and/or to recharge a power source associated with the device. As previously noted, techniques generally employ a primary coil driven by an external power source.

SUMMARY

Techniques are disclosed for transcutaneously transferring energy to recharge a rechargeable power source (e.g., a battery) of an implantable medical device (IMD). These techniques may involve inductive or RF coupling of a primary coil of an external device to a secondary coil of an IMD to transfer energy to the rechargeable power source of the IMD. To transfer energy as efficiently as possible, it may be desirable to tune the frequency of the signal being generated within the primary coil. Such tuning may occur before recharge is initiated and/or one or more times during the recharge session.

The optimal frequency at which to drive the primary coil may be based, in part, on the electrical properties of the antenna containing the primary coil as well as the other circuitry associated with the primary coil. This optimal frequency may further depend on the environment in which the antenna is placed. That is, the environment can present an additional inductance that "loads" the primary coil, resulting in a system resonant frequency that is likely different from the nominal resonant frequency of the antenna itself. The loading of the primary coil may change based on a changing shape of the primary coil (e.g., if the coil is flexible), a current location of the primary coil, and a current posture of a patient in whom the IMD is implanted.

In accordance with the foregoing, techniques are disclosed for determining a system resonant frequency for a recharge system. These techniques may involve monitoring a signal associated with the primary coil. If the system is not being driven at the system resonant frequency, characteristics may appear in this monitored signal that would not otherwise be present when the primary coil is being driven at the system resonant frequency.

According to one example, a charging system is disclosed that is configured to deliver power transcutaneously. The charging system comprises a primary coil, a drive circuit to drive the primary coil at a drive frequency, and a control circuit to tune the drive frequency based on a characteristic of a monitored signal that is associated with the primary coil. The characteristic is not present when the primary coil is being driven at a resonant frequency of the system.

In a specific example, an edge detect circuit is provided to detect a characteristic in the monitored signal. The characteristic may be described as one or more transitions that would not otherwise be present in the monitored signal at resonant frequency. Such transitions may define, for instance, a "stub pulse" appearing at a node of the tank circuit that includes the primary coil.

In some embodiments, the control circuit may be configured to change the frequency at which the drive circuit is being driven based on relative timing between the characteristic (e.g., the stub pulse) and another characteristic of the monitored signal, wherein this other characteristic of the monitored signal may be, for instance, a voltage pulse that is always present in the monitored signal whether or not the circuit is being driven at resonant frequency. In some cases, the control circuit is configured to decrease the drive frequency if the characteristic that is being monitored (e.g., stub pulse) appears within a predetermined time period of this other characteristic of the signal. Otherwise, if the stub pulse appears outside of the predetermined time period of this other characteristic, the frequency of the signal may be increased.

In some examples, the control circuit is configured to change the drive frequency by an amount that is based on the characteristic. For instance, in some cases, a width of the stub pulse will increase as the drive frequency departs further from the system resonant frequency. Thus, the amount by which frequency is adjusted to return to the system resonant frequency may be based on the stub pulse width.

In other embodiments, the control circuit is configured to increase a duty cycle at which the primary coil is being driven until the characteristic first appears in the signal at a first frequency and to adjust the drive frequency until the characteristic disappears and reappears at a second frequency. The control circuit may then adjust the drive frequency to be the average of the first and the second frequencies.

In other examples, the control circuit may be configured to determine a high frequency at which the characteristic first appears in the signal and a low frequency at which the characteristic first appears in the signal. The control circuit may then adjust the drive frequency to be the average of the high and the low frequencies. The control circuit may be configured to begin adjusting the drive frequency at a frequency f(outer) at which the characteristic appears. Each such adjustment may adjust the drive frequency by a predetermined increment. The control circuit may be configured to determine at least one of f(outer) and the predetermined increment during calibration of the system. The drive circuit may also be adapted to enforce a dead period during which the primary coil is not being driven, with the characteristic appearing in the monitored signal during this dead period.

In still other embodiments, the system may include a cable coupled to the primary coil. The control circuit may be carried by the cable. The system may also include a programmer to exchange at least one of data and programmed instructions with the IMD, with the control circuit being removably attached to the programmer.

Other examples provide a system comprising a circuit to generate a signal associated with transcutaneously delivering power. The circuit may be configured to tune the signal to a resonant frequency of the system based on a characteristic in the signal that is not present when the signal is at the resonant frequency of the system. The circuit may comprise an edge detector to detect the characteristic.

Still other embodiments relate to a method of transcutaneously delivering power. The method includes driving a primary coil, monitoring a signal associated with the primary coil, and adjusting a drive signal that is driving the primary coil to a resonant frequency based on a characteristic in the monitored signal that is not present when the drive signal is at the resonant frequency. The method may further include adjusting a frequency of the drive signal based on relative timing between the characteristic that is not present when the drive signals is at resonant frequency and another characteristic of the monitored signal that is present when the drive signal is at the resonant frequency.

Still other examples include a system comprising coil means for transcutaneously delivering power to the implantable medical device means. Such coil means may include a primary coil of the various embodiments described herein. The system may include signal generation means for generating a signal in the coil means and control means for tuning a frequency of the signal based on a characteristic of the signal that is not present when the coil means is driven at a resonant frequency of the system. Such signal generation means may comprise an H-bridge circuit according to examples described herein or other signal generation circuits as described herein. Control means may include control circuits of the various types and having the various structures described herein. The system may further comprise implantable medical device means for at least one of delivering a therapy to a patient or sensing a signal from the patient. Such implantable medical device means may comprise any of the implantable device applications described herein, including means for providing stimulation to a patient and means for delivering a therapeutic agent to the patient.

Other aspects of the disclosure will become apparent from the following description and the accompanying drawings.

DETAILED DESCRIPTION

Figure 1:
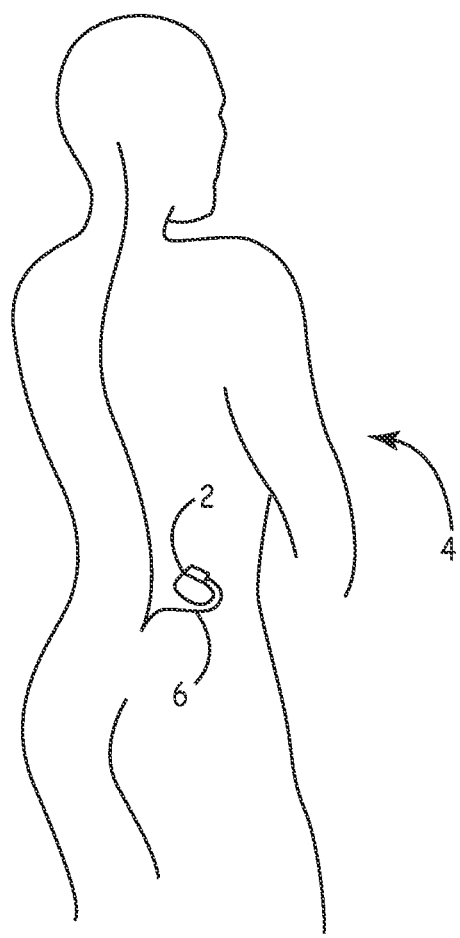
FIG. 1 is a diagram illustrating an exemplary implantable medical device.

Techniques are disclosed for transcutaneously transferring energy to an implantable medical device (IMD). The IMD may have a rechargeable power source coupled to a secondary coil. An external device having a primary coil positioned in proximity to the secondary coil may transfer energy transcutaneously to the secondary coil for use in recharging the rechargeable power source.

It is desirable for the energy transfer between the primary and secondary coils to be as efficient as possible. If the transfer is not efficient, recharging of the rechargeable power source will be more time-consuming, possibly inconveniencing the patient. Moreover, if the energy transfer is not efficient, more energy may be dissipated in the form of heat, which may be uncomfortable for the patient.

To increase efficiency of the energy transfer, the frequency at which the external device drives the antenna that contains the primary coil may be tuned. The optimal frequency at which to drive the antenna is based, in part, on the electrical properties of the antenna and related circuitry. This frequency further depends on the environment in which the antenna is placed. That is, the environment can present an additional inductance that "loads" the primary coil, resulting in a system resonant frequency that is likely different from the nominal resonant frequency of the antenna. Moreover, as the electrical characteristics of the environment change, the resonant frequency of the system also will likely change. As a result, even if frequency tuning was performed at the start of a recharge session, the system resonant frequency may change during this recharge session so that additional tuning is necessary to maintain optimal efficiency.

To locate the system resonant frequency in a very efficient manner, one aspect of the disclosure takes into account signal characteristics that are occurring within the tank circuit, wherein the tank circuit may comprise the primary coil and a tuning capacitor. These signal characteristics will change depending on whether the tank circuit is being driven at the resonant frequency. In particular, when the tank circuit is being driven at resonant frequency, the voltage waveform appearing at one or more nodes of the tank circuit will have a frequency that is substantially the same as the frequency at which the tank circuit is driven. However, if the tank circuit is not being driven at the resonant frequency of the system, additional characteristics will appear in this monitored voltage waveform that are not present at resonant frequency. In one embodiment, these characteristics may be described as "stub pulses" that comprise additional rising and falling edges not otherwise present when the circuit is being driven at resonant frequency.

An "extra" edge in the waveform (e.g., a stub pulse) of the type described above can be detected and used to very efficiently adjust the drive frequency to match the current resonant frequency of the system. In particular, the relative timing associated with a stub pulse will indicate whether the drive frequency must be increased or decreased to match the current resonant frequency of the system. This tuning can be completed in just a few cycles, allowing the system to remain at optimal efficiency during recharge even while the primary coil may be flexing and/or moving relative to the secondary coil. As one example, when the primary coil is being driven at a frequency above the resonant system frequency, stub pulses may appear within a predetermined time period of another voltage pulse in the monitored voltage signal. Conversely, when the primary coil is being driven at a frequency below the resonant system frequency, stub pulses will appear outside of this predetermined time. Thus, the relative timing of the stub pulse with respect to characteristics of the overall voltage signal can be used to determine whether to increase or decrease the frequency to locate the system resonant frequency.

Using the observations discussed above, tuning to locate an optimal frequency for performing recharge may be completed very quickly. In particular, a frequency f(high) may be determined at which stub pulses first appear because the primary coil is being driven above the system resonant frequency. Similarly, a frequency f(low) may be determined at which stub pulses first appear because the primary coil is being driven below the system resonant frequency. In one example, by taking the average of f(high) and f(low), the resonant frequency of the system may be approximated. Various mechanisms are available for using the stub pulses to determine the resonant system frequency.

The appearance of stub pulses may optionally be used to determine not only the type of frequency adjustment (e.g., increase versus decrease), but also the size of the adjustment. In particular, in some examples, the width of the stub pulses increase as the degree of tuning mismatch increases, thus allowing the size of the required adjustment to be estimated based on the stub pulse width.

Using the principals described herein, frequency tuning may be performed at various times before and/or during a recharge session in one embodiment. In one scenario, tuning is only performed once when a recharger is first paired with a patient. This tuning will determine a resonant frequency that may take into account the patient's body type, the depth of implant, the orientation of the secondary coil within the patient's body, and so on. The resonant system frequency resulting from the tuning may be recorded for use during all future recharge sessions. Alternatively, frequency tuning may be performed at the start of each recharge session to take into account a current location of the primary coil with respect to the secondary coil, a patient's current posture, etc. In yet another example, tuning may be reinitiated periodically throughout a recharge session, if desired, to account for changes in antenna position and body posture.

In one embodiment, the system may monitor recharge conditions to determine when re-tuning is needed. For instance, the system may monitor for the appearance of stub pulses, which may indicate the resonant frequency of the system has changed. Such an event may generate an interrupt or be detected by a polling mechanism. In either case, frequency re-tuning may be accomplished substantially in real-time so that an optimal recharge frequency is maintained despite coil flexing, coil movement and/or movement of the patient.

As noted above, the appearance of stub pulses may be used to determine not only a type of adjustment (increase versus decrease), but may also be used to determine an estimated amount of frequency increase or decrease needed to reach the system resonant frequency. This is because the width of a stub pulse will increase as the degree of mismatch between drive frequency and the system resonant frequency increases. Therefore, the determined relative width of a stub pulse can be used to estimate an amount by which frequency must be changed to allow this frequency tuning to be completed even more efficiently.

Other conditions may likewise be used to trigger frequency re-tuning, such as a change in a condition within the IMD (e.g., a sudden drop in current flowing to the rechargeable power source) or some other monitored condition within the IMD. This condition may be communicated to the external device via telemetry, for instance.

Frequency tuning as described herein may be performed while the antenna is stationary relative to the secondary coil. In fact, it may be desirable for the antenna to be positioned in the optimal location for performing recharge before frequency tuning is initiated. The optimal location may be that location that will result in the largest current being delivered to rechargeable power source at a given power level. Therefore, according to the current disclosure, mechanisms are provided to locate a secondary coil relative to a primary coil to perform recharge.

One way to determine optimal antenna location for recharge may involve receiving telemetry communications from the IMD that communicates data indicating the quality of coupling between the primary and the secondary coils. Examples of data that indicate coupling quality include current within the secondary coil, a voltage across the secondary coil, a current being delivered to the rechargeable power source, and a voltage associated with the rechargeable power source. For instance, it may be determined that at least an adequate antenna location has been found when a predetermined power level is being supplied to the primary coil and the current flowing into the rechargeable power source of the IMD reaches some predetermined minimum threshold value. This information may be used to provide feedback to a user (e.g., via a user interface of the external device) to indicate if and/or how the antenna should be moved to achieve optimal or near-optimal recharge efficiency. Of course, this approach may be used only when telemetry communication is available to provide information regarding the coupling quality.

According to one aspect, when telemetry communication cannot be established, as may occur when a zero-volt battery within the IMD has been nearly or fully depleted, the frequency tuning mechanism described above may be used to locate an optimal, or at least an adequate, location for the antenna. As one example, the external device may drive the antenna at a frequency that was previously determined to be system resonant frequency when the antenna was positioned at an optimal or near-optimal antenna location for performing recharge. Such a frequency may have previously been determined, for instance, when the antenna location was established with the aid of telemetry at a time when the power source of the IMD was not depleted. Once the antenna is being driven at this previously-established resonant frequency, the antenna may be moved around the vicinity of secondary coil. During this movement, the existence and size of stub pulses associated with the tank circuit may be monitored. The optimal location may be the position that does not result in any stub pulses at this drive frequency. The processing required to complete this determination may be performed very quickly such that feedback is provided in near real-time.

In one embodiment, the user may be provided with feedback based on whether the stub pulses are widening or narrowing. For instance, if current movement is causing the pulses to widen, feedback may be provided indicating direction of movement should be reversed. Similarly, if the pulses are narrowing, some indication may be provided that the user is "homing in" on the optimal location. Many mechanisms and types of feedback are possible, as discussed above.

In another embodiment, the resonant frequency can be determined using methods described herein. This frequency determination can occur substantially in real-time as the antenna is moved in the vicinity of the secondary coil. The location yielding the highest resonant frequency may be determined to provide the best recharge coupling quality (and hence provide substantially the largest recharge current being provided to the rechargeable power source of the IMD).

Still other mechanisms for locating an IMD having a depleted battery are described. According to one aspect, a voltage-based locating approach monitors a voltage within a drive circuit of the external device. In one example, the monitored voltage is a voltage being provided to an H-bridge circuit of the external device that drives the tank circuit. According to this locating method, the tank circuit may be driven at a predetermined frequency and duty cycle. The voltage supplied to the H-bridge circuit is then adjusted to achieve a predetermined current level within the tank circuit. In one example, the predetermined frequency, duty cycle, and current level can be established during a calibration process. Then the user may "sweep" the antenna over the general area of the IMD. As the antenna is moved, the voltage being delivered to the H-bridge circuit is automatically adjusted to maintain the predetermined current level in the tank circuit. This voltage will incrementally increase as the antenna is moved closer to the optimal location for performing recharge, since at this optimal location, loading of the primary coil by the secondary coil will also increase. The maximum voltage will be obtained at the optimal recharge location. Feedback concerning the voltage may be provided to the user to indicate a manner in which the antenna may be moved to obtain an optimal location for performing recharge. Using this voltage-based locating approach, a maximum power level will be transferred to the primary coil when the antenna is positioned at the optimal recharge location, which is one benefit of using this mechanism.

Another aspect of this disclosure relates to not only tuning frequency, as may be performed before, and during recharge, but also to tuning the power being delivered to primary coil 76 during recharge. Control of this power may be necessary to control heat dissipation within the recharge antenna, including the primary coil, as well as heat dissipation within the IMD. In one embodiment, this heat dissipation should be maintained below regulatory limits, manufacturer specifications, and/or patient preferences.

One direct way to determine heat dissipated by the primary coil and the IMD is through the use of temperature sensors which can measure the respective temperatures associated with the primary coil and IMD and ensure that power being delivered to the primary coil is reduced when either temperature limit is reached.

In another example, the heat dissipation associated with the primary coil and IMD may instead be calculated rather than measured, as follows. The power that is supplied to the primary coil ends up in one of several places: it is either dissipated as heat in the primary coil, it is supplied to the rechargeable power source of the IMD, or it is dissipated as heat within the IMD. The amount of heat dissipated in the primary coil is a function of the series AC resistance of the primary coil and the current in the primary coil. The series AC resistance of the primary coil is a known value that can be empirically determined or otherwise calculated, and in one embodiment, the current in the primary coil can be measured. The amount of power being supplied to the rechargeable power source of the IMD can be determined by measuring the current supplied to the rechargeable power source and the voltage of this power source. These values can be communicated via telemetry to the external device. Finally, the total power supplied to the primary coil is a function of the current in, and voltage supplied to, the primary coil, as well as the cosine of the phase differential between these two signals, all of which can be determined via measurements in one embodiment. Thus, the only unknown value is the heat dissipated by the IMD, which can be calculated using the other three values, all of which may be determined in the foregoing manner.

Once the heat dissipated within the IMD has been determined, it may be determined whether this value, or the value for the heat dissipated in the primary coil, exceed any respective limits, such as regulatory or manufacturer limits or patient preferences. If so, the power being provided to the primary coil can be reduced based on the limiting one of the heat dissipation values. This can be accomplished by reducing the voltage being supplied to the drive circuit of the primary coil and/or by reducing the duty cycle at which the drive circuit is being driven. Conversely, if both of the heat dissipation values are below respective limits, it may be desirable to increase the power being supplied to the drive circuit so that the time to complete recharge can be shortened. This can be accomplished by increasing the voltage being supplied to the drive circuit of the primary coil and/or by reducing the duty cycle at which the drive circuit is being driven. In one example, this "tuning" of the power can be performed in an on-going basis throughout a recharge session to ensure that recharge completes as efficiently and quickly as possible without heating limits being exceeded.

It will be appreciated, therefore, that the current disclosure sets forth techniques for performing frequency tuning that allows recharge to be accomplished in an efficient manner. Additional techniques are provided to locate the primary recharge coil with respect to the secondary coil so that adequate recharge coupling between primary and second recharge coils may be achieved. Still other techniques are provided to adjust power delivery during recharge so that recharge is carried out in a manner that is both efficient and comfortable for the patient.

FIG. 1 shows an exemplary IMD 2 that may take advantage of techniques disclosed herein. IMD may be adapted to deliver a type of therapy to the patient, which may include electrical stimulation and/or drug therapy. Many types of implantable medical devices may utilize the disclosed recharging systems and techniques, including implantable therapeutic substance delivery devices, implantable drug pumps, cardiac pacemakers, cardioverters or defibrillators, and/or devices to deliver electrical stimulation pulses for a neurological or muscular condition. Other specific examples include devices to provide therapy to treat chronic pain, tremor, Parkinson's disease, epilepsy, urinary or fecal incontinence, sexual dysfunction, obesity, or gastroparesis. Such therapy may be delivered via one or more therapy connections 6, which may be one or more leads and/or catheters. The patient's body may carry additional IMDs which may be similar to, or different from, IMD 2.

Figure 2:
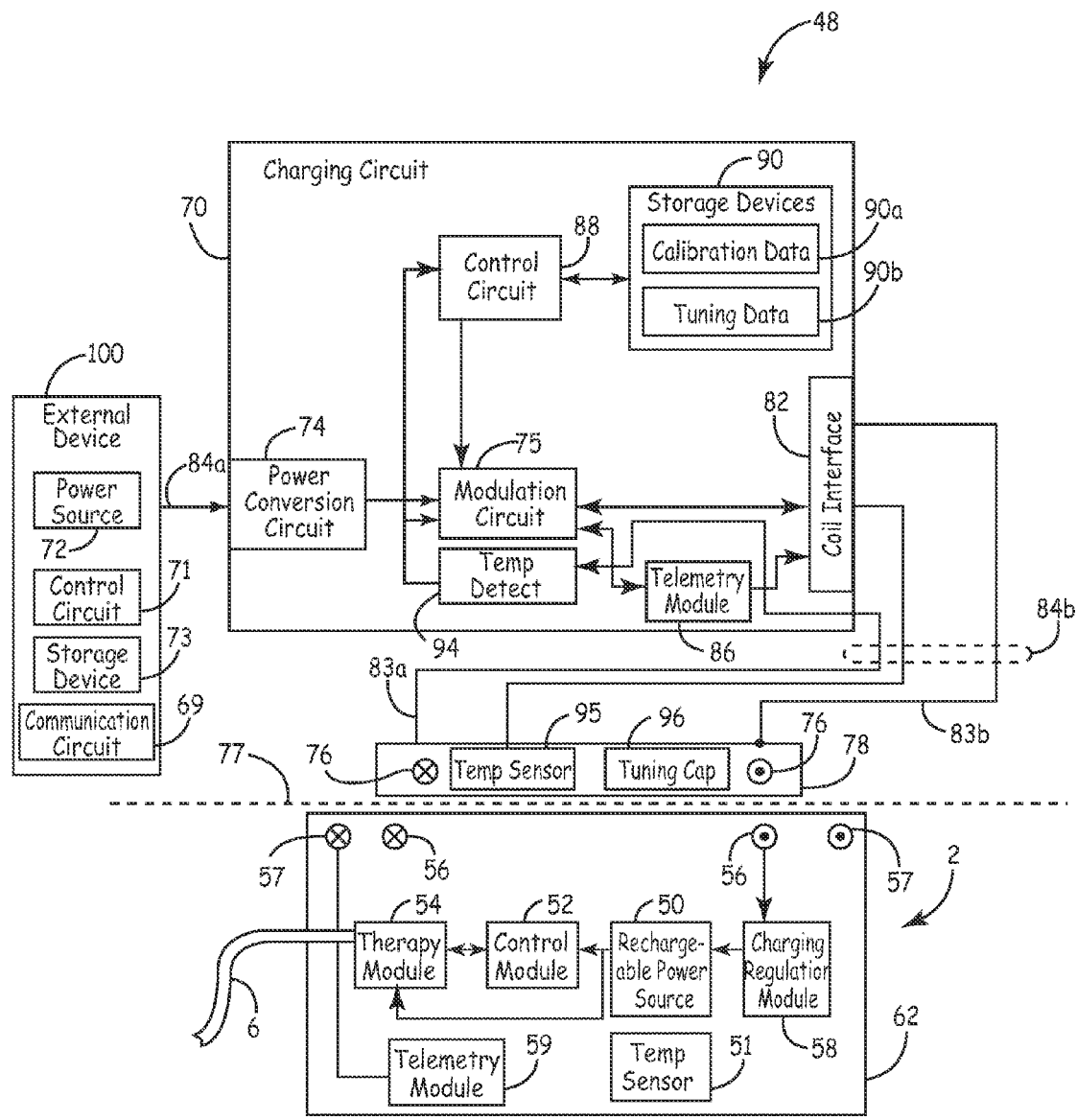
FIG. 2 is a block diagram of one embodiment of the implantable medical device of and a charging system for recharging a power source of the implantable medical device.

FIG. 2 is a block diagram of an exemplary charging system 48 that may usefully employ one or more of the techniques disclosed herein to recharge IMD 2. IMD 2 includes a rechargeable power source 50. Rechargeable power source 50 may be chemically-based (e.g., a battery) or may be a device to store charge (e.g., a capacitor). In one embodiment, rechargeable power source 50 is a lithium ion battery. Any other type of rechargeable power source suitable for powering an IMD may be used in conjunction with the mechanisms of the current disclosure.

Rechargeable power source 50 may be coupled to a control module 52, which includes circuitry to control therapy delivered to the patient. Control module 52 may include one or more processors, application-specific integrated circuits (ASICs), digital signal processors (DSPs), field-programmable gate arrays (FPGAs), discrete electronic components, state machines, sensors, memory, and/or other circuitry. The functions attributed to processors described herein may be embodied in firmware, hardware or any combination thereof. Control module 52 may further be coupled to therapy module 54, which delivers some form of therapy to a patient. This therapy may include controlled delivery of a substance and/or electrical stimulation. For example, in one embodiment, therapy module 54 may include one or more output pulse generators such as capacitive elements, voltage regulators, current regulators, voltage sources, current sources, and/or switches that are coupled to rechargeable power source 50 directly or through control module 52. Therapy module 54 may deliver electrical pulses to patient 4 via a combination of electrodes. As shown in FIG. 1, therapy module 54 may be coupled to patient 4 through one or more therapy connections 6 such as leads and/or catheters. Alternatively or additionally, the can of IMD 2 may carry or otherwise provide one or more electrodes for delivering therapy. As yet another possibility, IMD 2 may wirelessly communicate with and/or control one or more other implantable devices (e.g., microdevices) within the patient's body that likewise provide therapy and/or obtain sensed signals.

In one embodiment, rechargeable power source 50 may be coupled to a secondary coil 56 (shown in cross-section) through a charging regulation module 58. During a recharge session, a current is induced in secondary coil 56 which is provided to charging regulation module 58, which controls the charging of rechargeable power source 50.

IMD 2 may also include a telemetry module 59 coupled to a dedicated telemetry coil 57 (shown in cross-section) or telemetry may be performed using secondary coil 56 for both recharge and telemetry. Telemetry module 59 may utilize various types of telemetry protocols to communicate with external charging circuit 70. For example, a proximity telemetry system may be utilized for telemetry distances of 5 centimeters or less. An arm's length telemetry system may be employed for distances around, and in some cases more than, one meter. This latter type of system may utilize the electric field (E-field) component of a propagating wave to transmit information (e.g., the MICS band set aside for medical device telemetry.) Arm's length telemetry may also be achieved using the magnetic (H-field) component or coupled-coil transmission. Distance telemetry systems using E-field communication may be employed when separations between the antenna and the target device exceed arm's-length.

Rechargeable power source 50, charging regulation module 58, control module 52, therapy module 54, telemetry module 59, secondary coil 56 and telemetry coil 57 may be contained in a hermetically sealed housing 62. Alternatively, secondary coil 56 may be attached to, or positioned on, an exterior surface of sealed housing 62, or may be umbilically-coupled to the IMD via a cable. In one embodiment, a magnetic shield may be positioned between secondary coil 56 and other electronics to substantially increase the amount of energy captured by the secondary coil and protect the electronics from electromagnetic energy when secondary coil 56 is utilized to charge rechargeable power source 50.

IMD 2 may also include one or more sensors such as temperature sensor 51. Temperature sensor 51 can be used to ensure that heat dissipation does not exceed predetermined limits during recharge, for instance. This is discussed further below.

As previously discussed, FIG. 2 further illustrates a charging system 48 for recharging rechargeable power source 50 of IMD 2. Charging system 48 includes a charging circuit 70 that may receive power from a power source, which will be described further below. The power from this power source is provided to power conversion circuit 74, which supplies appropriate power levels to modulation circuit 75.

Modulation circuit 75 is a signal generator to generate a recharge signal of a desired frequency, typically somewhere between 8 KHz and 500 KHz. In one embodiment, modulation circuit 75 comprises a drive circuit to drive the primary coil 76, which may be an H-bridge circuit or a signal generator, for instance. The recharge signal may be a sine wave or some other type of signal, if desired. The frequency of the recharge signal may depend on the resonant frequency of the system, which takes into account the loading placed on the system when secondary coil 56 is inductively coupled across cutaneous boundary 77 (shown dashed) to primary coil 76. The frequency of the recharge signal may be varied during a charging session to find the resonant frequency of the system which will result in optimal charging efficiency, as will be discussed further below. In one specific embodiment described herein, the resonant frequency is substantially around 41 KHz.

The signal generated by modulation circuit 75 may be provided to drive primary coil 76 via coil interface 82 and signal lines 83a and 83b. Primary coil 76 may be of many different configurations. The size, shape, and number of turns of the coil will generally be selected based on the size and shape of secondary coil 56, as well as the implant scenario associated with IMD 2. For instance, primary coil 76 may be selected to be of a similar size and shape as secondary coil 56. This will generally result in better inductive coupling between coils and will typically provide better energy transfer to the rechargeable power source 50.

The number of turns of the primary coil 76 may be selected based on the likely implant depth and orientation of the IMD within a patient. For instance, if IMD 2 will likely be employed in an implant scenario involving a deep or angled implant, or if the coils are to be retained at some distance from cutaneous boundary 77 during recharge, it may be desirable to utilize a primary coil having an increased number of turns, which, in turn, will increase the magnetic field produced by this coil when the coil is driven with a given input signal. This increases magnetic field strength, as may be necessary to achieve adequate inductive coupling between the primary coil 76 and the secondary coil 56 in these types of situations. A larger number of turns may likewise be needed if primary coil 76 is intended for placement at some distance from cutaneous boundary 77 instead of being placed directly on this boundary, as may be applicable for some implant scenarios. For instance, this may be the case when an insulator or a cooling device is positioned between the primary coil 76 and the cutaneous boundary 77.

The configuration selected for primary coil 76 (e.g., size, shape, number of turns) will determine the inductance of the primary coil. In one specific embodiment, the inductance of primary coil is between 1.2 and 1.3 millihenries. This inductance, along with the capacitance and resistance of the system will, in turn, affect the resonant frequency at which the system is most efficiently driven. To tune the system so that this resonant frequency is at, or near, some predetermined desired resonant frequency, a tuning capacitor 96 having a selected capacitance may be electrically coupled to coil 76. For instance, this tuning capacitor may be coupled in series or in parallel with coil 76. In one example, tuning capacitor 96 may be a 12 nanofarad (nF) capacitor, thereby resulting in a self-resonant frequency of the antenna that is nominally 41 KHz. Of course, many other frequencies may be selected as the resonant frequency with the value of the tuning capacitor 96 being selected accordingly as is known in the art.

Coil and tuning capacitor 96 may be housed within an antenna 78, which may be a structure made of a material that is an electrical insulator. For instance, it may be made of a polymer that has a comfortable texture suitable for placement against the skin of the patient. Various types of polymers, including silicones, polypropylene, and urethanes may be used for this purpose. In one embodiment, antenna 78 is made of a thermally-conductive elastomer material that is capable of spreading heat generated by coil 76 over a wider surface to increase patient comfort during recharge.

In some examples wherein tuning capacitor 96 is coupled in series with coil 76, when coil 76 is being driven with an oscillating signal, as will occur during recharge, the node electrically coupling capacitor 96 to coil 76 will "ring up" to a high-amplitude voltage. Positioning the tuning capacitor 96 within antenna 78 will ensure that this high-voltage node is well insulated by the electrically-insulating material used to form antenna. An alternative embodiment may locate tuning capacitor 96 within circuit 70 that is situated remotely from antenna 78. This would place the high-voltage node within interface 84b (shown dashed), which may not be desirable if a cable that embodies this interface is damaged. Such a scenario may pose a shock risk. Thus one embodiment places tuning capacitor 96 within antenna 78 to avoid risk of shock.

Charging circuit 70 may have a telemetry module 86 enabling communication with IMD 2 during a charging session to provide status or other information concerning the charging session. Telemetry module 86 may utilize various types of telemetry protocols, including a proximity protocol for telemetry distances of 5 centimeters or less or an arm's-length telemetry protocol for distances of up to, or even exceeding, 1 meter. In one specific embodiment, telemetry module 86 is adapted to utilize a proximity protocol to communicate with IMD 2 via a coil within the IMD. In one embodiment, secondary recharge coil 56 may transmit/ receive telemetry communications to/from primary coil 76. Alternatively, a dedicated telemetry coil (e.g., telemetry coil 57) may be provided within IMD 2 for this purpose, as previously described. As yet another example, a longer-range telemetry protocol may be used by telemetry module 86 to communicate with IMD via a coil or some other type of antenna within the IMD.

In one embodiment, charging circuit 70 may be automatically activated using a telemetry signal received from IMD 2. For instance, charging circuit 70 may continuously send out requests via telemetry communication. When IMD 2 is in proximity to rechargeable power source 50, IMD 2 sends an acknowledgement to these requests so that charging circuit 70 may automatically initiate a recharge session without user intervention. Alternatively, the recharge session may be initiated upon user request or some other interaction between IMD 2 and charging circuit 70.

Charging circuit 70 may be controlled by control circuit 88, which may include one or more processors, FPGAs, ASICs, DSPs, microsequencers, discrete components, and/ or other electronic circuit components. The term "processor" or "processing circuitry" may generally refer to any of the foregoing logic circuitry, alone or in combination with other logic circuitry, or any other equivalent circuitry which may, but need not, include storage devices such as embedded memory devices. Some or all of the information necessary for the operation of charging circuit 70 may also be embodied or encoded in a computer-readable medium, such as a computer-readable storage medium, containing instructions. Instructions embedded or encoded in a computer-readable storage medium may cause a programmable processor, to perform the functions associated with control circuit 88, e.g., when the instructions are executed.

Control circuit 88 may automatically provide control signals to indicate how modulation circuit 75 is to drive primary coil 76, for instance. In an embodiment wherein control circuit 88 operates according to programmed instructions, control circuit 88 may be coupled to one or more storage devices 90, or may otherwise include such storage devices 90. These storage devices may include volatile, non-volatile, magnetic, optical, and/or electrical media for storing digital data and programmed instructions, including random access memory (RAM), read-only memory (ROM), non-volatile RAM (NVRAM), electrically erasable programmable ROM (EEPROM), flash memory, removable storage devices, and the like. In some implementations, charging circuit 70 may include a device interface that provides for transfer of data from charging device 70 to another device for storage. For example, charging device 70 may store data on a networked storage device through a network interface, or to a local storage device using a universal serial bus (USB) interface Storage devices 90, as well as any other storage devices discussed herein, may be considered, in some examples, a non-transitory computer-readable storage medium comprising instructions that cause one or more control circuits, such as, e.g., control circuit 88, to implement one or more of the example techniques described in this disclosure. The term "non-transitory" may indicate that the storage medium is not embodied in a carrier wave or a propagated signal. However, the term "non-transitory" should not be interpreted to mean that storage devices 90 are non-movable. As one example, storage device 90 may be removed from charging circuit 70, and moved to another device. In certain examples, a non-transitory storage medium may store data that can, over time, change (e.g., in RAM).

In one embodiment, charging circuit 70 may include a temperature detection circuit 94. This circuit receives one or more signals from at least one temperature sensor 95 that may be carried by antenna 78 and is in proximity to coil 76. Temperature sensor 95 provides one or more signals to temperature detection circuit 94 to allow the charging circuit 70 to determine whether temperature limits are being met during recharge. Such limits may be based on government regulations, patient preferences, and/or some other standard, and in some cases may be user-selectable (e.g., programmably selectable by a clinician or patient). If a detected temperature is exceeding a predetermined limit, temperature detection circuit 94 will provide a signal to control circuit 88. This may cause control circuit 88 to alter the signal driving the antenna 78 so that the temperature of the antenna will be reduced to within acceptable limits.

Charging circuit 70 receives energy from a power source, which in one embodiment, may be selectable by the user to be any one or more of an AC wall outlet, rechargeable batteries (e.g., lithium ion batteries) or prime cell batteries. Such batteries may be housed with charging circuit or housed in a separate device.

In the illustrated scenario, the power source is power source 72 that is housed within an external device 100. This external device may be a patient or clinician programmer used to exchange data (e.g., programming commands, patient information, status information, etc.) with IMD 2 and/or provide recharge capabilities. In one example, external device 100 provide some control during recharge to modulate the level of power provided by charging circuit 70 to IMD 2 to limit tissue heating, as will be described below.

External device 100 may couple to charging circuit 70 over interface 84a. This interface may be a cable that removably plugs into a connector of the external device. Such a configuration allows charging circuit 70 and coil 76 to be removably coupled to the external device 100. The connector provided for this purpose may be designed according to an industry-standard (e.g., Universal Serial Bus standard) or may be a proprietary-type connector.

External device 100 may include a control circuit 71 comprising one or more processors, Application Specific Integrated Circuits (ASICS), state machine logic, software, firmware, and/or any type of logic known in the art. Control circuit 71 may provide some level of control to charging circuit 70 in one embodiment, as will be described below.

External device 100 may further include one or more storage devices 73 for storing programmed instructions such as firmware and/or software, control parameters, patient data, programming parameters to control operation of IMD 2, and any other instructions and/or data needed to aid in control of charging circuit, IMD and/or external device 100. For instance, in some examples, instructions stored within storage devices 73 may control execution of control circuit 71. Storage device(s) 73 may include volatile, non-volatile, magnetic, optical, and/or electrical media for storing digital data and programmed instructions, including random access memory (RAM), read-only memory (ROM), non-volatile RAM (NVRAM), electrically erasable programmable ROM (EEPROM), flash memory, removable storage devices, and the like.

External device 100 may also include a communication circuit 69 for communicating with telemetry module 59 of IMD 2 and/or telemetry module 86 (as may be desirable when external device 100 is not coupled via interface 84a to charging circuit 70). In one example, communication circuit 69 may provide short-range inductive telemetry and/or longer range RF telemetry.

Communication circuit 69 may further provide the capability to communicate with another external device such as a recharger, a programmer or computing device via a wired or wireless connection using any of a variety of local wireless communication techniques, such as RF communication according to the IEEE 802.11 or Bluetooth® specification sets, infrared (IR) communication according to the IRDA specification set, or other standard or proprietary telemetry protocols. Further, external device 100 may communicate via a local area network (LAN), wide area network (WAN), public switched telephone network (PSTN), or cellular telephone network, for example.

In some implementations, external device 100 may include a device interface that provides for transfer of data from the external device 100 to another device for storage. For example, external device 100 may store data on a networked storage device through a network interface, or to a local storage device using a universal serial bus (USB) interface. In this manner, external device 100 may also communicate with other programming or computing devices via exchange of removable media, such as magnetic or optical disks, or memory cards.

Figure 3:
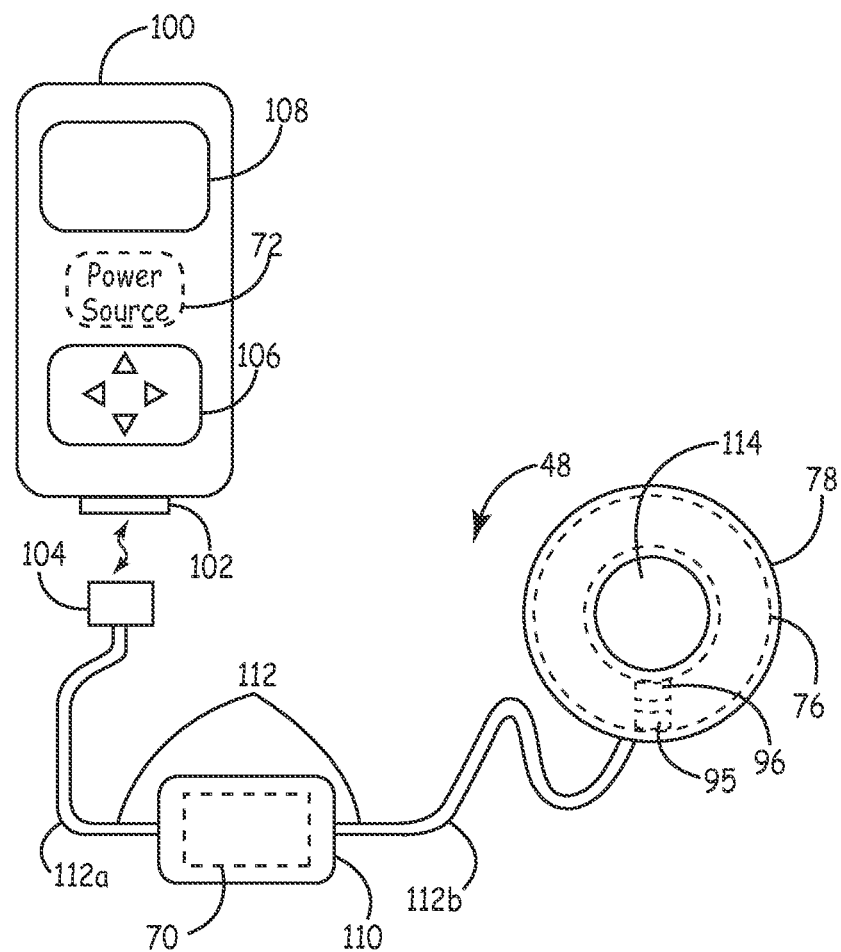
FIG. 3 is an example system representation of the charging system of FIG. 2

FIG. 3 is a system representation of one example of the charging system 48 of FIG. 2 coupled to an external device 100, which may be a patient programmer. Such a programmer may be employed by a user to perform programming and monitoring tasks associated with IMD 2, as is known in the art. For instance, the programmer may be used to initially configure the IMD after implant, to modify therapy that is being delivered to the patient, to obtain data from the IMD indicative of patient, therapy, and/or system status, and so on.

External device 100 may have a user interface 108 such as a display screen that may include a key pad 106. The user interface may include color and touch-screen capabilities and/or any other user interface mechanisms known in the art. As discussed above, patient programmer may be powered by power source 72 (shown dashed), which may be a prime cell battery, a rechargeable battery and/or a circuit designed to couple to a wall outlet. This power source may provide charging circuit 70 (shown dashed) with the power and ground signal levels needed for circuit operation.

In one embodiment, charging circuit 70 may be removably coupled to external device 100. In particular charging circuit 70 may be electrically coupled to a cable 112 comprising cable portions 112a and 112b. This cable may be equipped with a connector 104 that plugs into connector 102 of external device 100. Connectors 102 and 104 may be of many types. In one embodiment, the connectors comply with electrical and/or mechanical aspects set forth in an industry standard specification, such as the electrical characteristics outlined by the Universal Serial Bus (USB) Specification. Alternatively or additionally, the connectors may have one or more aspects that conform to a proprietary format.

In some embodiments, connector 104 of cable 112 may be adapted to interface with multiple types of external devices that provide standard voltage and ground connections utilized by connector 104. For instance, if connector 104 has standard voltage and ground connections specified by the USB specification, any type of external device that is adapted to mechanically receive connector 104, that provides these standard voltage and ground connections, and that is capable of satisfying the power requirements of charging circuit 70 may be used to power recharger.

According to one aspect, external device 100 may be adapted to detect when it has been coupled to charging system 48 and respond accordingly. For instance, this may involve automatically presenting a user interface display via screen 108 that provides the capabilities to allow a user to initiate a recharge operation, as may be accomplished by selecting appropriate key strokes of keypad 106, engaging a touch screen interface, or using some other user interface mechanism. Thus, by merely plugging charging system 48 into connector 102, external device 100 automatically becomes configured for use in performing the recharge operation without any additional interaction on the part of the user such as the need to navigate to an appropriate recharge screen to initiate this operation.

Charging circuit 70 may be housed within a circuit module 110 that is carried by cable 112. Specifically, a portion 112a of cable 112 provides interface 84a (FIG. 2) coupling external device 100 to charging circuit 70. A second portion 112b of cable 112 provides interface 84b (FIG. 2) coupling charging circuit 70 to antenna 78.

Circuit module 110 may, but need not, provide some capability to receive user input and/or to provide feedback to the user. Such user input capability may include one or more buttons that may be employed by a user to initiate recharge or to activate a locate function in advance of initiating recharge. Circuit module 110 may include other capabilities to allow for user interaction, such as a display screen or other visual indicators (e.g., LEDs or LCDs), voice activated control, touch screen capabilities, or any other user input mechanisms described above with respect to external device 100 and/or known in the art.

Circuit module 110 may be of many different shapes and sizes. In one embodiment, it may be a tubular component that is wider than the rest of cable 112. In one instance, the components shown included within charging circuit 70 in FIG. 2 may all reside within circuit module 110. In other embodiments, any one or more of the components shown to be included within charging circuit 70 may instead reside within external device 100. In yet additional embodiments, components in addition to those shown in FIG. 2 may be housed within circuit module 110. In alternative embodiments, one or more of the circuit components shown in FIG. 2 to be included within charging circuit 70 may be located within antenna 78.

Allowing one or more of the circuit components of charging circuit 70 to be carried by circuit module 110 rather than external device 100 has advantages. For instance, the circuitry needed to drive antenna 78 will generally be tailored to drive a specific antenna configuration, as discussed above. For instance, modulation circuit 75 and/or control circuit 88 may be configured to drive an antenna having a particular resonant frequency and loading characteristics. When housed within circuit module 110, this circuitry will be attached to, and "travel with", the antenna for which it is designed, rather than being incorporated into a specific external device. This eliminates the need to have different versions of an external device, each being adapted to drive a corresponding antenna configuration and/or to recharge a particular type of implantable medical device. The external device need only have the appropriate connector and expected power and ground levels to drive any number of antenna configurations that can be used with a variety of implantable medical devices. Additionally, locating circuitry within circuit module 110 rather than within antenna 78 helps to minimize the size, weight, and profile of the antenna. This may make the antenna easier for the patient to handle. Further, heat generated by charging circuit 70 may be readily dissipated when carried on the cable without contributing to heating of antenna 112 during recharge.

In one example, the modularity of charging system 48 may be even further enhanced. That is, antenna 78 may be removably-connected to cable portion 112b, which in turn may be removably connected to circuit module 110. Circuit module 110 may likewise be removably-connected to cable portion 112a. This "plug-and-play" capability allows various circuit modules to be coupled to a range of antennas so that systems may be more specifically tailored for a type of implant. For instance, the system may be tailored for a specific type of implant device by selecting size and shape of the primary coil. The system may further be tailored for an appropriate implant scenario (e.g., implant depth, angle of implant) by selecting a circuit module having the capability for a particular drive strength.

In the type of modular system described above, the length of cable portions 112a and 112b may, in one case, be selected based on user preferences so that circuit module 110 may be located in a desired position relative to antenna 78. For instance, some users may prefer that circuit module 110 is located closer to antenna 78 so that this object is less likely to be swinging freely during recharge. Other users may want the circuit module to be located closer to connector 104, possibly allowing this module to be carried within a pocket of a jacket or otherwise carried by clothing. In one embodiment, circuit module 110 may even have clips or hooks to allow fastening this module to clothing in some fashion. In one particular embodiment, cable portion 112a is about half the length of cable portion 112b so that circuit module 110 is one-third the distance from external device 100 to antenna 78.

Cable 112 may be a shielded cable having an external insulating jacket that may be formed of nylon, urethane, silicone, rubber, or some other insulating material. In one embodiment, it is formed of Santoprene® thermoplastic rubber having a durometer of about 70 Shore.

Turning now to a discussion of antenna 78, as previously discussed, this component may carry at least one temperature sensor 95 (shown dashed) and/or a tuning capacitor 96 (shown dashed). An advantage of locating the tuning capacitor in proximity of coil 76 is that in an in-series configuration, the high voltage node between the capacitor 96 and coil 76 will be well-insulated and protected by antenna 78 rather than being located within cable portion 112b (as would occur if the capacitor were included within charging circuit 70). This latter embodiment may pose a risk of shock to the patient if cable portion 112b is damaged.

The configuration of antenna 78 illustrated in FIG. 3 includes a center opening 114 to allow air to flow within the center of coil 76, and also decreases the thermal mass of this element. This may aid somewhat in heat dissipation and also reduce the weight of antenna 78. Of course, many other configurations are possible, including antennas that are solid structures without such openings.

While the foregoing discusses a separate external device 100 coupled to a cable that carries charging circuit 70, this is just one example of how the system may be configured. In another example, charging circuit 70 is contained within a same housing as power source 72, and the separate external device 100 may be eliminated. For instance, the charging circuit 70 may be part of a dedicated recharger.

Such a recharger may be portable or may instead be a stationary unit. For instance, a stationary recharger may be positioned at a location know to be frequented by the patient so that recharging may be initiated passively without patient interaction whenever the patient is within range of the unit. In another embodiment, charging circuit may be an integral part of a patient or clinician programmer.

It is important that energy transfer between primary coil 76 and secondary coil 56 be as efficient as possible. If the transfer is not efficient, recharging rechargeable power source 50 will require more time, possibly inconveniencing the patient. Moreover, if the energy transfer is not efficient, more energy may be dissipated in the form of heat. Some of this heat may be absorbed by tissue in the proximity of antenna 78 or IMD 2, leading to patient discomfort.

Efficiency of the energy transfer may be improved by adjusting the frequency and duty cycle at which primary coil 76 is driven during recharge. The optimal frequency at which to drive antenna 78 is based, in part, on the electrical properties of antenna 78. In one embodiment, the antenna includes a primary coil 76 having an inductance of between 1.2 and 1.3 millihenries and a tuning capacitor 96 selected to be 12 nF, thereby resulting in a self-resonant frequency of the antenna that is nominally 41 KHz. However, this inductance of the antenna will change with flexing.

Optimal frequency at which to drive antenna 78 further depends on the environment in which the antenna is placed. That is, the environment can present an additional inductance that "loads" the coil 76 of antenna 78. When the electrical characteristics of the environment change, the self-inductance of antenna 78 may remain constant while the mutual inductance, which includes the interaction between coil 76 and the environment, may change. Thus, the resonant frequency of the system may change as the environment changes. As a result, even if the antenna is being driven at its self-resonant frequency, this may not be the system resonant frequency. Therefore, energy will not be transferred to implantable medical device 2 as efficiently as possible, since maximum efficiency occurs when the drive frequency matches the system resonant frequency.

To locate the system resonant frequency in a very efficient manner, one aspect of the disclosure takes into account signal transitions that are occurring within the tank circuit. These signal transitions will change depending on whether the tank circuit is being driven at the resonant frequency. This will be described in more detail in reference to the circuit diagram of FIG. 4.

Figure 4:
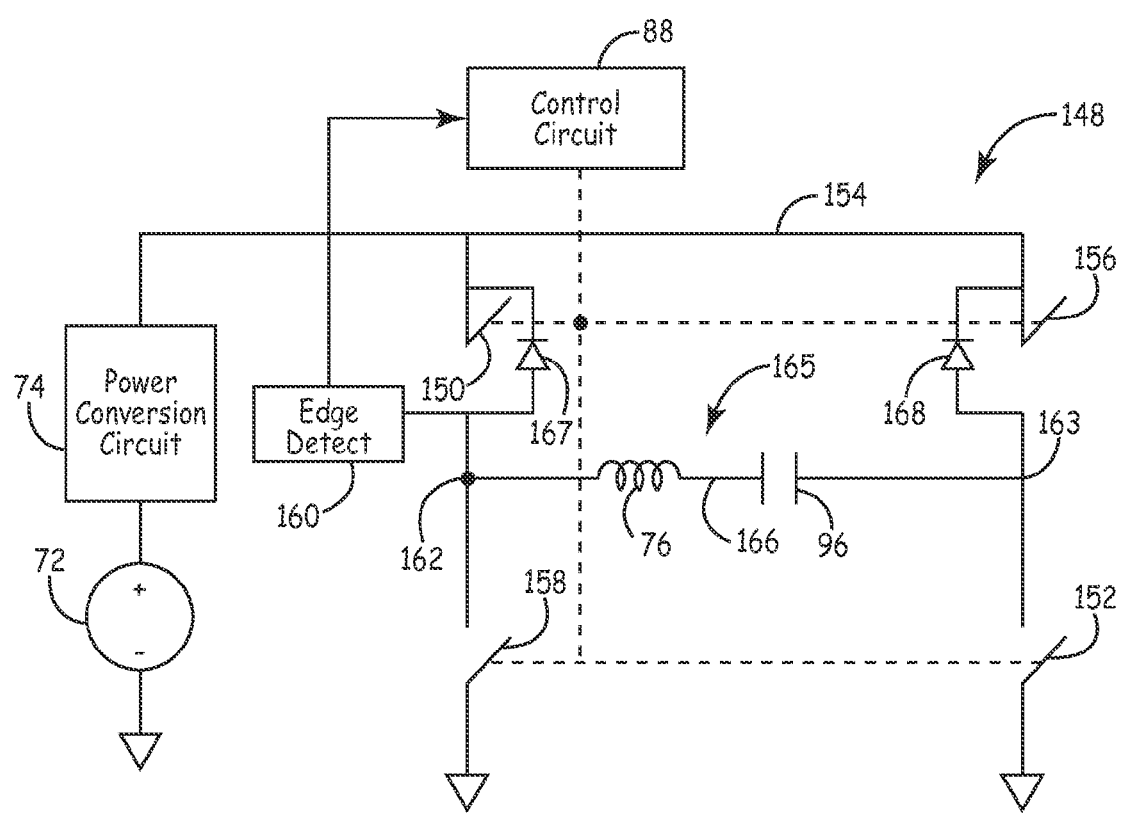
FIG. 4 is a diagram of an example circuit that may be used to transcutaneously deliver power to the implantable medical device.

FIG. 4 is a diagram of a circuit that may be used by charging device 70 of FIG. 2. An H-bridge circuit 148 of the type known in the art comprises four switches 150, 152, 156, and 158, which may be Field-Effect Transistors (FETs), Micro-Electro-Mechanical (MEMS) switches, or some other type of switch controllable by control circuit 88.

The circuit includes a power source 72 and power conversion circuit 74. As previously described, power source may be a prime cell or rechargeable battery, or some other power source. In a specific example, power source 72 provides a voltage level of between 7 and 8 volts to power conversion circuit. Power conversion circuit 74 is a boost circuit that may boost the voltage level received from power source 72 to a DC voltage of between 8 and 12 volts in one embodiment, which is a voltage that may be used for operation of H-bridge circuit 148.

The H-bridge circuit 148 is employed to generate a signal in the tank circuit 165, wherein the tank circuit comprises tuning capacitor 96 and primary coil 76. Specifically, control circuit 88 generates drive signals to gate switches 150 and 152ON for a predetermined period of time, thereby allowing current to flow from node 154 through switch 150 and the tank circuit 165 and finally to ground through switch 152. Sometime thereafter, switches 150 and 152 are gated OFF and switches 156 and 158 are gated ON. This allows current to flow from node 154 through switch 156 and the tank circuit 165, and finally to ground through switch 158. By generating drive signals to gate switch pairs 150, 152 and 156, 158 in this manner, the voltage at each of nodes 162 and 163 will approximate a sine wave. As noted above, the frequency of this signal will be determined based on the self-inductance of the tank circuit 165 as well as the mutual inductance of the system that additionally comprises the secondary coil 56 of the IMD.

The duty cycle of each switch pair cannot exceed 50%, since only one switch pair can be driven at a time without shorting power to ground. In fact, each switch pair must be driven at a duty cycle of somewhat less than 50% because the transition between closing one switch pair and opening another cannot occur simultaneously. To allow sufficient time for one switch pair to become non-conducting before gating another switch pair ON, there is an enforced "dead period" of time during which none of the switch pairs allow current to flow. During this dead period, at least one side of the tank circuit 165 is "floating", being coupled neither to ground nor to power. During this time, a "fly-back" voltage develops at a floating node of the circuit, which may be either node 162 or 163. In one embodiment, the amplitude of this fly-back voltage may be held to some predetermined maximum voltage by diodes 167 and 168 that are provided across switches 150 and 156, respectively. In another embodiment wherein FETs are used for the switches 150, 156, diodes 167 and 168 may be eliminated and the body diodes of the FETs may be relied upon to limit voltage at nodes 162 and 163. In yet another embodiment, both the body diodes of the FETs and additional diodes 167 and 168 may be used for this purpose.

If the tank circuit is not being driven at the resonant frequency of the system, current flowing through diodes 167, 168 and/or body diodes of FETs (in an embodiment wherein FETs are used for switches 150, 156) will result in the appearance of a signal characteristic in a voltage waveform appearing at node 162 or 163. This signal characteristic would not otherwise be present if the H-bridge were being driven at the resonant frequency of the system. In one example, this characteristic comprises a positive-to-negative going transition and a negative-to-positive-going transition that would not appear in the voltage waveform at the monitored node if the tank circuit 165 were being driven at resonant frequency. These transitions may, in one scenario, be described as "stub pulses" that appear on a voltage waveform detectable at node 162 and/or 163 of the circuit of FIG. 4.

A superfluous transition in the waveform (e.g., a stub pulse) of the type described above can be detected by detection circuit, which is monitoring this circuit node. In one example, the detection circuit is edge detect circuit 160, which provides an indication of the transition to control circuit 88. In other examples, a circuit may be provided that detects the stub pulse in a different way, such as by detecting a series of amplitude levels that has been associated with an approximate shape of a stub pulse.

Based on the output from the detection circuit, control circuit 88 is able to very efficiently adjust the drive frequency of the tank circuit 165 to match the resonant frequency of the system. In particular, the relative timing associated with any detected stub pulse will indicate whether control circuit 88 must increase or decrease the drive frequency to match the current resonant frequency of the system. This tuning can be completed in just a few cycles, allowing the system to remain at optimal efficiency during recharge even while the primary coil 76 may be flexing and/or moving relative to the secondary coil 56. The manner in which the system is tuned to the resonant frequency of the system is described in reference to FIGS. 5A-5C.

Figure 5A:
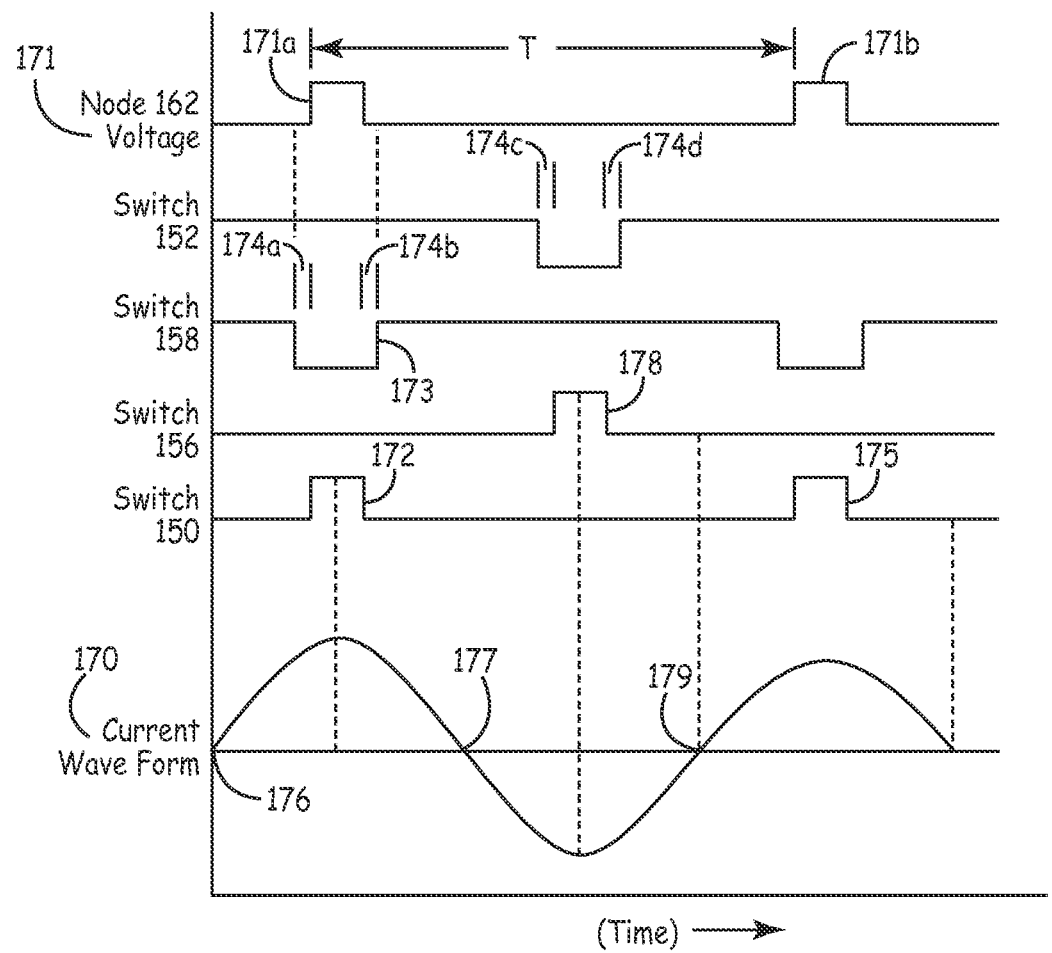
FIG. 5A is a timing diagram illustrating control of an H-bridge circuit that is substantially tuned to a system resonant frequency.

FIG. 5A is a timing diagram illustrating how control circuit 88 controls switches 150, 152, 156 and 158 to drive H-bridge circuit at the resonant system frequency. In this figure, the "switch 150" waveform illustrates the control signal (or "drive signal") used to gate switch 150ON/OFF, "switch 152" waveform illustrates the control signal used to gate switch 152ON/OFF, and so on, for each of the four switches of the H-bridge circuit. In this example, it is assumed that each of the switches is gated ON by a high-active signal level, however, it will be appreciated that one or more of the switches may be low-active instead in another example.

As discussed above and shown in FIG. 5A, the pair of switches 150 and 152 will be gated ON at a same time to allow current to flow from node 154 through switch 150 and the tank circuit 165 and finally through switch 152 to ground. This occurs, for instance, when pulse 172 is used to gate switch 150ON. Also at this time, the waveform for switch 152 shows switch 152 is likewise gated ON to permit this flow of current. During this time, switches 156 and 158 are OFF, as indicated by low-active pulse 173 of the switch 158 waveform and the corresponding low-active level illustrated by the switch 156 waveform. Current will flow through the pair of switches 150, 152 in the aforementioned manner for a time corresponding to the width of pulse 172. When pulse 172 ends, switch 150 is turned OFF such that current no longer flows through this switch pair 150, 152.

Sometime thereafter, switch 156 is gated ON, as indicated by pulse 178. This occurs at a time when switch 158 is already ON, as indicated by the high-active level illustrated by the switch 158 waveform during pulse 178. This allows current to flow in the opposite direction through tank circuit 165. This current flow continues for the duration of the high-active pulse 178.

Sometime thereafter, switch pair 150, 152 will again be driven. This occurs when switch 150 is again activated by high-active pulse 175. This process of alternating the switch pair that is ON generates a current in tank circuit 165 represented by current waveform 170 of FIG. 5A. This waveform will approximate a sine wave. For simplicity, the waveform is shown as a sine waveform, although it will be understood this is an approximation only.

The signals shown in FIG. 5A will have several characteristics when the H-bridge circuit is being driven at the resonant frequency of the system. First, the current signal within the tank circuit 165, as represented by current waveform 170, will approximate a sine waveform having a frequency that is at the resonant frequency of the system. The voltage across the primary coil 76 (not shown in FIG. 5A) will also be a signal occurring at the resonant system frequency. There will not be any phase difference between the voltage across the primary coil 76 and the current in the tank circuit (represented by waveform 170) at the resonant frequency. Additionally, at resonant frequency, pulses associated with control of the switches will be centered between zero crossings of the current waveform 170 in the manner shown in FIG. 5A. For instance, pulse 172 of the switch 150 waveform is shown centered between successive zero crossings 176 and 177 of current waveform 170. Likewise, pulse 178 of the switch 156 waveform is shown centered between zero crossing 177 and 179, and so on.

As discussed above, switches 150 and 158 cannot be ON at the same time or there will substantially be a short circuit between the voltage at node 154 and ground. Moreover, because a finite time is required to turn the switches ON and OFF, one of these switches cannot be turned ON at the same time the other switch is turned OFF. Thus, there are enforced "dead periods" between the time a control signal is deactivated to turn switch 158 OFF and the time a control signal is activated to gate switch 150ON, and vice versa. These "dead periods" are shown by time periods 174a and 174b in FIG. 5A. In particular, time period 174a is the minimum time from when the control signal for switch 158 transitions from high-active to low-inactive to the time when the control signal for switch 150 may transition from low-inactive to high-active. Conversely, time period 174b corresponds to the minimum time from when the control signal for switch 150 transitions from high-active to low-inactive to the time when the control signal for switch 158 may transition from low-inactive to high-active. During these times, node 162 is "floating", being neither pulled to the voltage of node 154 or to ground.

A similar observation may be made for switches 152 and 156: namely, the switches cannot be ON at the same time. Moreover, because a finite time is required to turn the switches ON and OFF, one of these switches cannot be turned ON at the same time the other switch is turned OFF, and there are enforced "dead periods" between the time a control signal is deactivated to turn switch 152 OFF and the time a control signal is activated to gate switch 156ON, and vice versa. These "dead periods" are shown by time periods 174c and 174d in FIG. 5A. In particular, time period 174c is the minimum time from when the control signal for switch 152 transitions from high-active to low-inactive to the time when the control signal for switch 156 may transition from low-inactive to high-active. Conversely, time period 174d corresponds to the minimum time from when the control signal for switch 156 transitions from high-active to low-inactive to the time when the control signal for switch 152 may transition from low-inactive to high-active. During these times, node 163 is "floating", being neither pulled to the voltage of node 154 or to ground.

When the H-bridge is being driven at resonant system frequency as is represented by FIG. 5A, the voltage at node 162 during dead periods 174a and 174b will remain at a low signal level. There will be no signal transitions (e.g., pulses) appearing during dead periods 174a and 174b. This is represented by waveform 171, which shows the voltage at node 162 substantially mirroring the signal controlling switch 150. That is, the voltage will be pulled substantially to the supply voltage of node 154 through switch when switch 150 is gated ON, and will instead be pulled to a low voltage level through switch 158 when this switch is gated ON. During the dead periods 174a and 174b when neither switch is gated ON, this signal at node 162 will remain at a low voltage level. As such, there will only be one voltage pulse, shown as pulse 171a occurring during the single period T of the drive signal. This is shown by waveform 171.

In the example circuit of FIG. 4, the voltage at node 162 may be monitored by edge detect circuit 160 to detect any occurrence of pulse edges during dead periods 174a and 174b. In the example shown in FIG. 5A, there are no edges occurring during dead periods 174a and 174b such that only a single rising or falling edge will be detected during the time period T by edge detect circuit 160 This will be the single edge associated with pulse 171a. Thus, this signal at node 162 will have a frequency matching the resonant frequency of the system. Based on the detection of only one edge during period T (i.e., because of the absence of any stub pulses), control circuit 88 may readily determine that the system is being driven at, or substantially at, the system resonant frequency.

While in one embodiment, edge detect circuit 160 need only detect either rising or falling edges of the voltage signal at node 162 to determine whether the H-bridge circuit is being driven at resonant frequency, in another embodiment, edge detect circuit may detect both rising and falling edges. This may be useful in determining a width of any stub pulses appearing during dead periods 174a and 174b, as will be discussed further below.

While the foregoing discusses detection of stub pulses by monitoring voltage node 162, a similar discussion applies for the voltage at node 163 (not shown in FIG. 5A). As previously discussed, the voltage at node 163 will be controlled based on the state of switches 152 and 156, with dead periods 174c and 174d being required between activation of these switches. The voltage at node 163 will, in one embodiment, somewhat mirror the signal controlling switch 156. That is, the voltage at node 163 will be pulled to the supply voltage of node 154 when switch 156 is ON, and will instead be pulled to a low voltage through switch 152 when switch 152 is ON.

When the tank circuit 165 is being driven at resonant frequency, there will be no additional pulses appearing in the voltage signal at node 163 during dead periods 174c and 174d in a manner similar to that shown for waveform 171 of node 162. That is, this signal at node 163 will likewise have a pulse frequency matching the resonant frequency of the system. Thus, it will be appreciated that an edge detect circuit positioned at node 163 could be used to detect stub pulses instead of, or in addition to, edge detect circuit 160 that is positioned at node 162. Thus, the description herein of edge detect circuit 160 at node 162 being used for this purpose is illustrative only and not limiting.

As previously described, when the H-bridge control signals (e.g., the control signals for switches 152, 154, 156, 158) are being driven at the resonant frequency of the system, both the current of the tank circuit (shown by current waveform 170) and voltage across primary coil 76 are also at resonant frequency. Moreover, these two signals will be in-phase with one another.

Figure 5B:
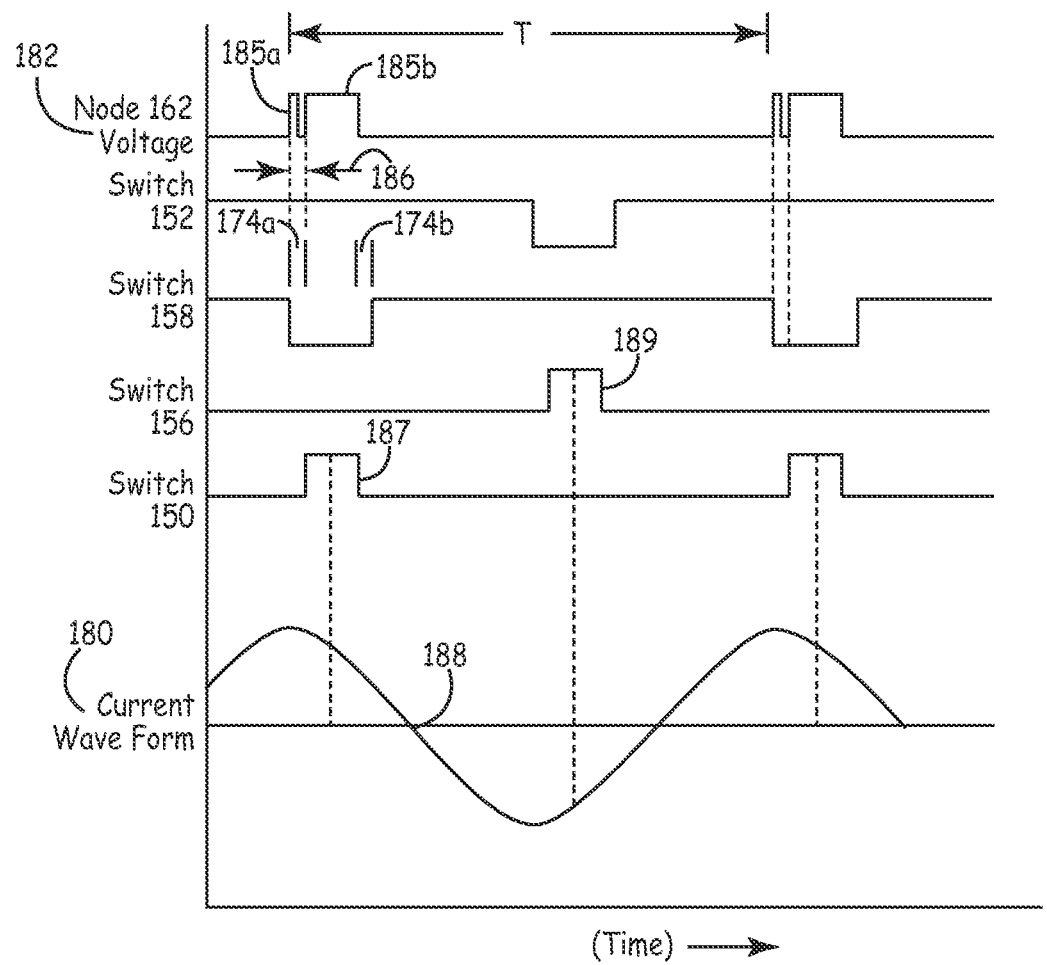
FIG. 5B is a timing diagram illustrating control of an H-bridge circuit that is being driven at a frequency that is greater than the system resonant frequency.

FIG. 5B is a timing diagram illustrating control of the H-bridge circuit of FIG. 4 when the H-bridge circuit is being driven at a frequency higher than the resonant frequency of the system. The waveforms of FIG. 5B correspond to similar waveforms of FIG. 5A. That is, the "switch 150" waveform illustrates the control signal used to gate switch 150ON/OFF, "switch 152" waveform illustrates the control signal to gate switch 152ON/OFF, and so on. Also similar to that of FIG. 5A, tank current waveform 180 represents current in the tank circuit 165, and waveform 182 represents the voltage at circuit node 162 of FIG. 4. As was the case with FIG. 5A, it is assumed that each of the switches is gated ON by a "high" signal level, however, it will be appreciated that the gating signals for one or more switches may be low-active instead in another example.

In the example of FIG. 5B, the H-bridge circuit is being driven at a frequency above the resonant frequency of the system. As such, a characteristic appears in the monitored tank circuit signal (i.e., the monitored voltage signal at node 162) that would not otherwise appear at resonant frequency. This characteristic may comprise additional negative-to-positive and positive-to-negative "transitions" or edges (e.g., shown as a stub pulse) appearing in the voltage signal. For example, stub pulse 185a is shown occurring during dead period 174a of waveform 182, preceding the "main" voltage pulse 185b. The "extra" pulse 185a will be detected by edge detect circuit 160. Thus, edge detect circuit 160 will detect two rising or two falling edges during the period T of the drive signal instead of one edge as would otherwise be the case if the H-bridge were being driven at resonant frequency in the manner shown in FIG. 5A.

In one embodiment, when the frequency is too high as illustrated by FIG. 5B, edges of two successive pulses (e.g. the rising edges of pulses 185a and 185b) will be separated in time by less than some predetermined time period indicated by arrows 186. In a specific example, this time period is less than or equal to the maximum dead period 174a.

As is also apparent from FIG. 5B, because the system is being driven at a frequency above the system resonant frequency, the control pulses for the H-bridge switches begin to shift relative to the current waveform 180. For instance, pulse 187 begins to shift towards the positive-to-negative-going zero crossing 188 of the current waveform 180 rather than being centered between two successive zero crossings as was the case in FIG. 5A.

Figure 5C:
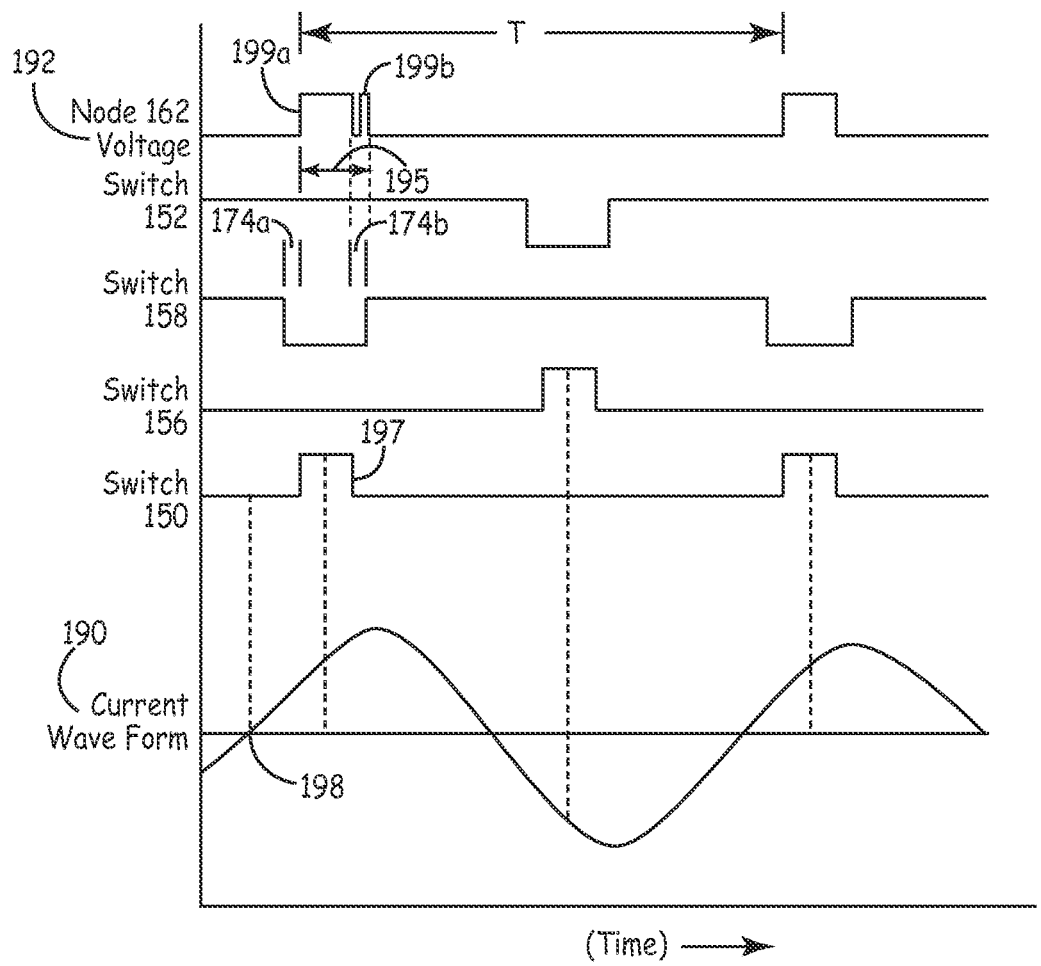
FIG. 5C is a timing diagram illustrating control of an H-bridge circuit that is being driven at a frequency that is lower than the system resonant frequency.

FIG. 5C is a timing diagram illustrating control of the H-bridge circuit of FIG. 4 when the H-bridge circuit is being driven at a frequency lower than the resonant frequency of the system. The waveforms of FIG. 5C correspond to similar waveforms of FIG. 5A. That is, the "switch 150" waveform illustrates the control signal used to gate switch 150ON/OFF, "switch 152" waveform illustrates the control signal to gate switch 152ON/OFF, and so on. Also similar to that of FIG. 5A, current waveform 190 represents the current in the tank circuit 165, and waveform 192 represents the voltage at circuit node 162 of FIG. 4. As was the case with FIG. 5A, it is assumed that each of the switches is gated ON by a "high" signal level, although this is illustrative only.

In the example of FIG. 5C, the H-bridge circuit is being driven at a frequency below the resonant frequency of the system. As such, a characteristic appears in the monitored tank circuit signal (i.e., the monitored voltage signal at node 162) that would not otherwise appear at resonant frequency. This characteristic may comprise additional negative-to-positive and positive-to-negative "transitions", or edges (e.g., shown as a stub pulse) appearing in the voltage signal. For example, stub pulse 199b is shown occurring during dead period 174b of waveform 192, following the "main" voltage pulse 199a. The "extra" pulse 199b will be detected by edge detect circuit 160. Thus, edge detect circuit 160 will detect two rising or two falling edges during the period T of the drive signal instead of one edge as will be the case when the H-bridge is being driven at resonant frequency.

In one embodiment, when the frequency is too low as illustrated by FIG. 5C, edges of two successive pulses of the monitored voltage signal (e.g. the rising edges of pulses 199a and 199b) will be separated in time by more than some predetermined time period, as indicated by arrow 195. In a specific example, the edges are separated in time by more than the maximum dead period 174a of the system.

As is also apparent from FIG. 5C, because the system is being driven at a frequency below the system resonant frequency, the control pulses for the H-bridge switches begin to shift relative to the tank current waveform 190. For instance, pulse 197 of the switch 150 waveform begins to shift towards the positive-to-negative-going zero crossing 198 of the current waveform 190 rather than being centered between successive zero crossings as was the case in FIG. 5A.

Using stub pulse detection according to principals discussed above, tuning to locate an optimal frequency for performing recharge may be completed very quickly. For example, a frequency f(high) may be determined at which stub pulses first appear in the manner shown in FIG. 5B because the H-bridge circuit is being driven above the system resonant frequency. Similarly, a frequency f(low) may be determined at which stub pulses first appear in the manner shown in FIG. 5C because the H-bridge circuit is being driven below the system resonant frequency. By taking the average of f(high) and f(low), the resonant frequency of the system may be approximated. Example methods of determining resonant frequency are discussed in the examples of FIGS. 6A and 6B.

Methods for determining system resonant frequency may be practiced before a recharge session is initiated and/or throughout the duration of a recharge session, if desired. During this time, the system may continue to monitor for the appearance of stub pulses. The appearance of such pulses may indicate whether the resonant frequency of the system has changed, as may occur because of flexing of the antenna 78, a change in the patient's posture, movement of antenna 78 relative to the patient, and so on. This may trigger re-tuning of the frequency.

Figure 6A:
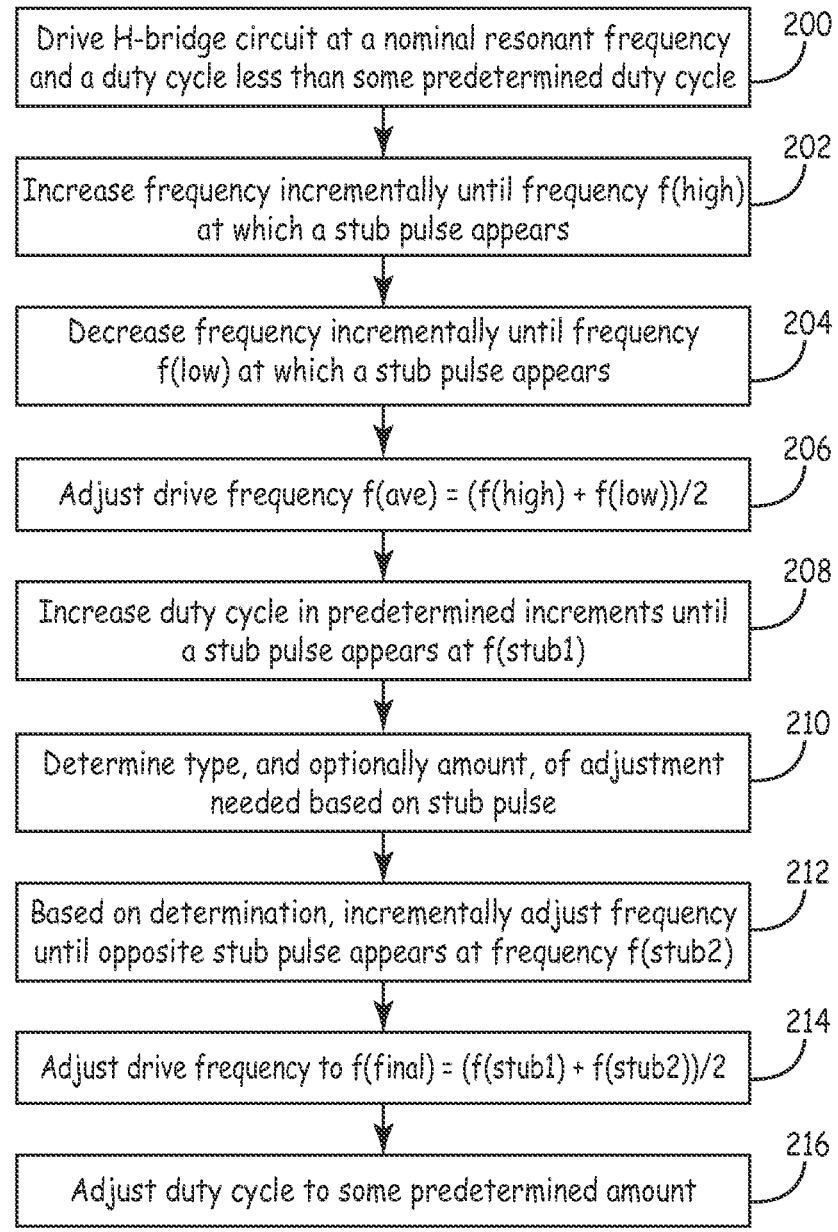
FIG. 6A is a flow diagram illustrating an example method of tuning a drive signal of an H-bridge circuit.

FIG. 6A is a flow diagram illustrating an example method that utilizes the concepts described above to tune the drive signals of H-bridge circuit 148 so that the H-bridge is driven at the system resonant frequency. When the H-bridge is driven at resonant frequency, the current of the tank circuit 165 and voltage across the primary coil 76 will also be at the resonant system frequency and no phase difference will exist between these signals.

According to this method, when a recharge session is initiated, the H-bridge circuit 148 may initially be driven at a nominal resonant frequency, which may be the frequency selected based on the self-resonance of the charging circuit 70, including antenna 78 (200). That is, the control signals that gate switches 150, 152, 156, and 158ON/OFF are being driven at this nominal resonant frequency, which in one example is 41 KHz. When initially driving the H-bridge circuit at this nominal resonant frequency, the duty cycle of the drive pulses are set to some predetermined duty cycle. In one embodiment, this predetermined duty cycle is relatively small to ensure that the edges of the drive pulses will not be approaching a zero crossing of the current in the tank circuit 165. For instance, in reference to FIG. 5A, by selecting the duty cycle of a signal driving switch 150 to be something well less than 50%, the leading edge of pulse 172 will not approach zero crossing 176, and a trailing edge of pulse 172 will not approach zero crossing 177. In one specific example, the initial duty cycle is selected to be 5%, but other values may be used in the alternative.

Next, the frequency of the drive signal is increased incrementally until a frequency of f(high) is attained, which is the frequency at which a stub pulse first appears near a predetermined zero crossing (202). As shown by waveform 182 of FIG. 5B, in one example, this stub pulse 185a will appear preceding a pulse (e.g., pulse 187) corresponding to the control signal pulse that gates switch 150ON. Recall that this stub pulse will result in edge detect circuit 160 detecting more than one edge per period T.

The incremental adjustment of the frequency to obtain a frequency that finally produces this stub pulse may occur in predetermined steps, if desired. For instance, the drive frequency may be changed in steps of between 5 Hz and 100 Hz. In a specific case, the frequency is changed between about 70 Hz and 92 Hz each step. As an example, the drive frequency may first be set to 41 KHz, incremented to 41.07 KHz, incremented again to 41.14 KHz, incremented yet again to 41.21 KHz, and so on, until a stub pulse is detected. Any frequency increment may be used for this purpose. The smaller the increment, the more accurate will be the final determined frequency. However, when a smaller increment is used, the tuning process will take longer to complete.

In an alternative embodiment, rather than altering the frequency of the drive signal by some predetermined amount during each step, the period of the drive signal may be changed by a predetermined time increment. For example, the period may be changed each step by an increment of between 10 nanoseconds (ns) and 100 ns. In a specific illustration, the period of the drive signal may be increment by 46 ns each step as the sweep progresses from a mid-frequency (e.g., 41 KHz) to f(high). This will result in a frequency delta that is not constant, but instead increases slightly as the frequency sweep progresses from low to high frequencies. For instance, initially, the frequency will change by about 70 Hz each step but this frequency delta will increase as f(high) is approached.

Once f(high) is determined, a similar process may be performed to determine a low frequency at which stub pulses appear. To accomplish this, control circuit 88 may again drive tank circuit 165 at the nominal resonant frequency (e.g., 41 KHz). In incremental steps, control circuit 88 may decrease the frequency of the drive signal until a frequency f(low) is reached (204). This is the frequency at which a stub pulse first appears as a result of the frequency decrease. Recall that this stub pulse 199b will be detected after a pulse 197 that gates switch 172ON, as shown in FIG. 5C, and will result in edge detect circuit 160 detecting more than one edge per period. The incremental adjustment of the frequency may again occur in predetermined frequency steps, such as some frequency step of between 5 Hz and 100 Hz. In a specific example, a frequency change of about 70 Hz may be used.

Alternatively, the period of the drive signal may be adjusted by a predetermined amount. For instance, the period may be incremented each step by between 10 ns and 100 ns so that the frequency decreases. This will result in a frequency delta that is not constant, but rather decreases slightly as the frequency sweep progresses from high to low frequencies.

The drive frequency is next set to a frequency f(ave), which is the average of the high and low frequencies, f(high) and f(low), which were determined in the preceding steps (206). At this frequency, no stub pulses should be appearing. If stub pulses do appear, the process of steps 202-206 must be repeated. At frequency f(ave), the pulses controlling the H-bridge switches should be substantially centered between zero crossings, as shown in FIG. 5A.

Recall that at this point, the duty cycle is still set to some predetermined duty cycle that is relatively small, such as 5%. In one example, it may be desirable to increase the duty cycle as much as possible while still maintaining the resonant frequency of the system. This may be desirable for several reasons. First, for a given voltage level, more power will be provided to the primary coil 76 at a higher duty cycle. This power will be available for transfer to secondary coil 56 for recharging rechargeable power source 50. While it would be possible to increase the voltage level supplied by power conversion circuit 74 to increase the power level, providing a power conversion circuit 74 that can increase the voltage in this manner may increase the complexity and/or expense of the system. Thus, it may be more desirable to instead increase the duty cycle, which is a simple operation controlled by control circuit 88.

Another reason it may be desirable to increase the duty cycle involves the speed at which stub pulses will appear when the circuit loses tuning. Specifically, when a larger duty cycle is in use, stub pulses will appear very quickly when the circuit is even slightly out of tune. This may allow the system to be very responsive to an off-tuned condition. This is discussed further below.

In view of the foregoing, in an embodiment that utilizes an increased duty cycle following the initial frequency tuning, the duty cycle of the drive pulses (e.g., the pulses supplied to switch pair 150, 152) may next be incrementally increased (208). This incremental increase may occur by some predetermined amount, such as by 2 or 5 percent each step. Alternatively, it may be increased more at first (e.g., by 5%), and later incremented by smaller amounts (e.g., by 2%) after some mid-point duty cycle is reached (e.g., when the duty cycle reaches 30%.) Many examples are possible. In any event, after each such increase in the duty cycle of the drive pulses, it may be determined whether a stub pulse has appeared. The incremental increase in the duty cycle continues until frequency f(stub1) is attained, which is the frequency at which a stub pulse first appears. This stub pulse could be either one that is associated with either dead period 174a or 174b of FIGS. 5A-5C in an embodiment wherein monitoring at node 162 is occurring.

Based on the location of the stub pulse that is appearing at drive frequency f(stub1), a determination may be made as to how to adjust frequency (210). According to one example, if the two detected edges are separated in time by less than some predetermined maximum time period, frequency should be decreased, as described above in reference to FIG. 5B. In one example, the predetermined maximum time period is a maximum dead period 174a or 174b of the system. In other words, if edge detect circuit 160 detects two edges separated in time by no more than time 174a, frequency should be decreased. In contrast, if the edge detect circuit 160 detects two edges within period T of the drive signal that are separated in time by more than time 174a, frequency should be increased, as shown in FIG. 5C.

As also shown in step 210 of FIG. 6A, the stub pulse may optionally be used to determine not only the type of frequency adjustment (e.g., increase versus decrease), but also the size of the adjustment. In particular, in some examples, the width of the stub pulse increases as the degree of tuning mismatch increases, thus allowing the size of the required adjustment to be estimated. This is discussed further below.

Based on a determination of the type of frequency adjustment required in step 210 (i.e., increase versus decrease), another incremental adjustment to the drive signal may be performed (212). For instance, if the relative timing of the stub pulses is similar to that shown in FIG. 5B, indicating the frequency is now too high, the adjustment should incrementally decrease the frequency. In contrast, if the relative timing of the stub pulses is similar to that shown in FIG. 5C, indicating the frequency is now too low, the adjustment should incrementally increase the frequency. In any event, this adjustment may occur in relatively small steps that involve a predetermined frequency adjustment. For instance, each step may adjust frequency by 1 Hz or some other relatively small amount. Alternatively, the adjustment could occur by changing the period of the drive signal by a predetermined time increment each step. As a result of these adjustments, the sub pulses will first disappear and then finally reappear at a second frequency f(stub2).

As an example of the foregoing, if step 210 determined that a reduction in frequency is needed, the frequency may be reduced a predetermined frequency amount each step (e.g., by 5 Hz) or by increasing the period by some time period each step (e.g., by 10 ns). After each such step, it is determined whether frequency has been slowed so much that a stub pulse 199b has now appeared after a "main" voltage pulse 199a, as shown in FIG. 5C. If so, this frequency is considered f(stub2).

Alternatively, if step 210 determined that an increase in frequency is needed, the frequency may be increased a predetermined frequency amount each step (e.g., by 5 Hz) or the period may be decreased by some predetermined amount each step (e.g., by 10 ns). After each such step, it is determined whether frequency has been increased so much that a stub pulse 185a has now appeared before a "main" pulse 185b, as shown in FIG. 5B. If so, this frequency is considered f(stub2).

Next, the H-bridge drive frequency is adjusted to the final frequency f(final), which is the average of f(stub1) and f(stub2) (214). The duty cycle may be set to some final predetermined maximum value (216). In one embodiment, this final value may be 40% for a single switch pair (or 80% for both switch pairs.) Other values may be selected in the alternative based on system parameters. Alternatively, the duty cycle may be left set to the value used during tuning, which may be substantially less than 40% in some examples.

It will be appreciated that in any of the steps described herein involving the recording of a frequency (e.g. f(high), f(low), f(stub1), or f(stub2)), the drive signal period may instead be recorded and used to determine a final frequency or period of the drive signal. For instance, the period at f(high) and at f(low) may be recorded and averaged in step 206. Control circuit 88 may then drive tank circuit 165 based on this determined period, with the same result being achieved. Recording frequency to perform tuning is therefore an arbitrary choice, and the period of the drive frequency could be used instead.

The final drive signal may provide optimal power transfer at the resonant frequency of the system. This may minimize the amount of energy wasted, thereby conserving energy of power source 72. This wasted energy will not be lost as heat, which might otherwise be dissipated into the surrounding environment, possibly heating tissue and leading to patient discomfort. Moreover, by increasing the duty cycle in step 208 to widen the drive pulse, the system may become more sensitized to stub pulses such that even a small deviation from the resonant system frequency will result in the appearance of stub pulses. This will allow re-tuning to occur very quickly so that resonant frequency is maintained.

In one embodiment, control circuit 88 is a processing circuit that receives a notification (e.g., an interrupt) upon the first appearance of a stub pulse, allowing frequency re-tuning to be done in real-time so that optimal tuning is maintained despite flexing or movement of the coil, movement of the patient, and so on.

As noted above in regard to step 210 of FIG. 6A, the appearance of stub pulses may be used to determine not only a type of adjustment (increase versus decrease), but may also be used to determine an estimated amount of increase or decrease. This is because the width of a stub pulse will increase as the degree of mismatch between drive frequency and the system resonant frequency increases. Therefore, in one example wherein edge detect circuit 160 is capable of detecting both rising and falling edges, the relative width of a stub pulse (e.g., the time elapsed between rising and falling edges) may be determined. In one case, such a determination may be made by control circuit 88. The determined relative width of the stub pulse can be used to estimate an amount by which frequency must be changed. Thus, in one embodiment, step 210 may determine not only the type, but also an amount, of adjustment to make based on the stub pulse location and width, respectively. For instance, when a larger stub pulse indicates larger adjustments are to be made, those larger adjustments could be used for a first predetermined number of iterations to quickly "dial in" to the second stub frequency f(stub2). After this first predetermined number of adjustments, the size of the adjustments may be scaled back, if desired, so that f(stub2) is not "over-shot".

In some embodiments, the width of a stub pulse may increase so much that the stub pulse may "blend" with a main pulse. For instance, in FIG. 5B, stub pulse 185a may get so wide that stub pulse 185a and pulse 185b become one pulse. This type of situation can be detected by detecting both rising and falling edges of a signal pulse using an edge detect circuit 160 having this capability. From the timing associated with these two edges, it may then be determined that the pulse is larger than the corresponding drive signal pulse 187. Further because the timing associated with the drive signal is "known", in one example, it may be determined whether a rising edge of the pulse detected at node 162 precedes a rising edge of pulse 187, or whether the falling edge of this pulse instead trails the falling edge of pulse 187. In the former case, the drive frequency must be decreased in a manner similar to that described with respect to FIG. 5B. In the latter case, the drive frequency must be increased in the manner described in regards to FIG. 5C.

Other embodiments of the method of FIG. 6A are possible. For instance, the process of FIG. 6A may be initiated with a duty cycle that is considered "good enough" (e.g., 30%). Using this approach, steps 202-206 may be performed to find f(ave), and the process may be considered complete. This process may be completed more quickly than if the entire process, including steps 208-214, which are used to increase the duty cycle, are executed.

As another example, the H-bridge circuit may initially be driven with some nominal resonant frequency and a relatively small duty cycle as initially described in reference to step 200. Thereafter, processing may proceed directly to steps 208-214 where the duty cycle is incrementally increased to determine f(stub1), f(stub2) and f(final), with step 216 being considered optional. Such an embodiment may eliminate the iterations associated with steps 202 and 204. Thus, one skilled in the art will appreciate that many examples are possible. In some examples, steps may be re-ordered. Moreover, in examples, some steps may be eliminated entirely to increase a speed at which tuning may be performed. Thus, FIG. 6A is illustrative only.

The various methods described in reference to FIG. 6A discuss initiating the frequency sweep at a nominal resonant frequency that lies in a "tuned frequency range" wherein stub pulses are not generated. In another embodiment, the tuning process may instead commence at a frequency f(outer) that is outside of this tuned frequency range. Frequency f(outer) is selected to be a frequency at which it is known that stub pulses will reliably appear. That is, f(outer) is selected to be either below a low frequency at which stub pulses first appear (e.g., below f(low) of FIG. 6A) or above a high frequency at which stub pulses will first appear (e.g., above f(high) of FIG. 6A). A sweep may be performed to sweep from f(outer) towards the tuned frequency range until the frequency wherein stub pulses first disappear (f(disappear) is located. From there, the frequency sweep may continue through the tuned frequency range at which stub pulses are absent, and finally proceed to the frequency at which the stub pulses first reappear (f(reappear)). The frequency may then be set to the average of f(disappear) and f(reappear).

As discussed above in reference to FIG. 6A, the predetermined sweep from f(outer) through the tuned frequency range may occur by adjusting frequency by a predetermined frequency adjustment amount during each step. For instance the adjustment amount may be an increment of between 5 Hz and 100 Hz. Alternatively, the adjustment may occur by changing the drive signal period a predetermined time increment each step. For instance, some time increment of between 5 ns and 100 ns may be used for this purpose. Any frequency or time increment may be selected in any of the embodiments of FIGS. 6A and 6B, recognizing that a smaller increment will yield a more accurate final frequency determination but will result in a tuning mechanism that includes more steps and hence takes longer to complete.

The frequency sweep from f(outer) may commence above or below the tuned frequency range. If f(outer) is below the tuned frequency range, the frequency sweep will involve incrementally increasing the frequency (or incrementally decreasing the period) until a stub pulse first disappears. The sweep then proceeds through the tuned frequency range until the frequency at which a stub pulse first reappears is located. Conversely, if f(outer) is above the tuned frequency range, this process may involve decreasing the frequency by a predetermined frequency amount (or increasing the period by a predetermined time increment) until a stub pulse first disappears. This sweep is continued through the tuned frequency range until the frequency at which a stub pulse first reappears is located.

Some calibration procedure may be performed to initially determine the frequency f(outer) and/or the incremental frequency adjustment to use during the sweep. One method for calibrating f(outer) may utilize the steps of FIG. 6A to determine f(high) or f(low). The frequency f(outer) may then be selected to be some predetermined amount higher than f(high) or alternatively some predetermined amount lower than f(low). For instance, the predetermined amount may be 100 Hz such that f(outer) is selected to be 100 Hz lower than f(low) or 100 Hz higher than f(high). The predetermined frequency amount selected for determining f(outer) should be large enough to ensure that when the H-bridge circuit is driven at a frequency of f(outer), stub pulses will reliably appear. However, f(outer) should not be so far away from the corresponding borderline frequency (e.g., f(low) or f(high)) that the sweep time will be increased beyond an acceptable amount.

Many other methods may be used to determine f(outer). For instance, a "trial" low-to-high or a high-to-low frequency sweep may be performed around the known nominal resonant frequency of antenna 78 to determine f(disappear) and f(reappear). The frequency f(outer) may be selected to be some acceptable distance from one of these frequencies in the manner discussed above.

In a system wherein f(outer) can be selected to be either above or below the resonant frequency, the direction of the frequency sweep must be noted so that the process will complete successfully. One way to record this direction may involve allowing the frequency delta (i.e., the amount by which the frequency will be changed each step) to be either a positive value (for an increasing sweep) or a negative value (for a decreasing sweep). In one embodiment, the direction of the frequency sweep is merely "hard-coded" in the logic so that the sweep is always performed in one direction (e.g., low to high) with f(outer) being selected accordingly.

The size of the frequency increment used in the sweep may also be determined during the calibration procedure. This could be performed, for instance, by subtracting f(low) from f(high) and dividing by the number of incremental steps desired to step through this range during the frequency sweep, keeping in mind that additional steps will be needed to traverse the range from f(outer) to the frequency at which stub pulses first disappear. In one example, the frequency increment may be about 70 Hz. As discussed above, in one example, the frequency increment could be selected as a negative value to thereby result in a decreasing frequency sweep.

The selection of the incremental value must balance the need for accuracy against speed in completing the sweep. A more accurate resonant frequency will be obtained when using a smaller increment. Conversely, the time to complete the frequency sweep and perform tuning will be decreased if a larger increment is selected. In one embodiment, it may be desirable to use a larger increment in some situations wherein completing the tuning very quickly is necessary. A smaller delta value may be selected when tuning is to be performed more accurately and over a longer period of time. Once f(outer) and/or the frequency increment are determined during the calibration step, those values can be stored for later use.

In a very specific example, the frequency sweep begins at 39 KHz with pulses of 1000 ns being used to control switches 150 and 156 of the H-bridge circuit 148. The frequency sweep progresses upward through a nominal resonant frequency of 41 KHz until locating a frequency higher than 41 KHz at which stub pulses first re-appear. During this process, the drive signal period is decremented each step by about 46 ns to affect the frequency increase. In one example, no more than 63 steps are required to complete the sweep. During the sweep, the voltage at which the H-bridge is driven (i.e., the voltage at node 154) remains set to a predetermined voltage, which in one embodiment is 11 volts.

Figure 6B:
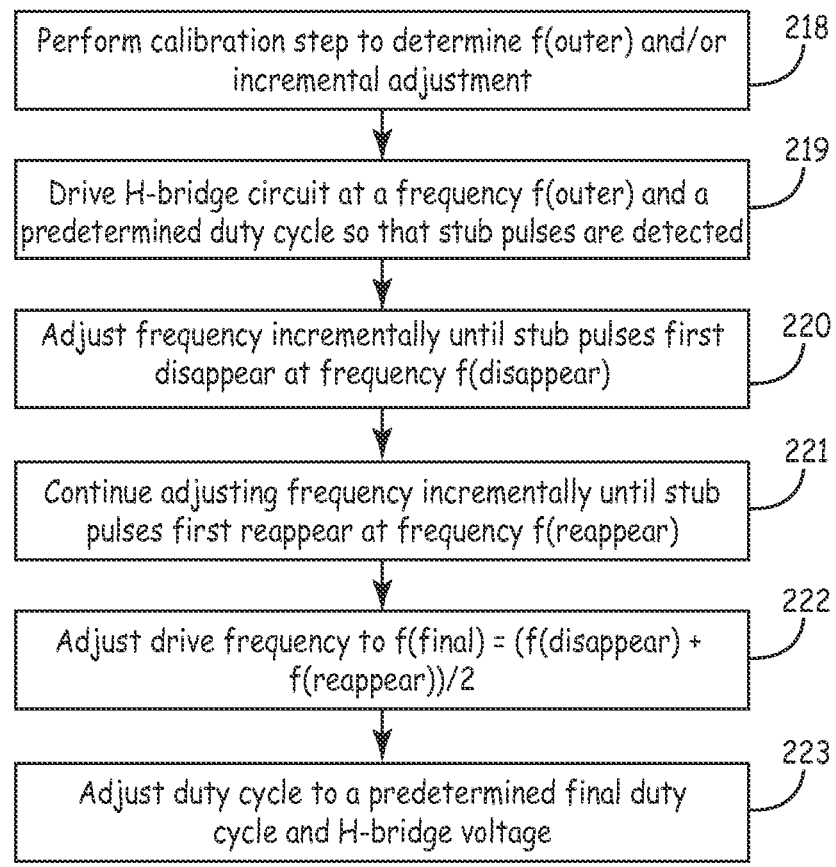
FIG. 6B is a flow diagram of another example method of tuning a drive signal of an H-bridge circuit.

FIG. 6B illustrates an example method of performing a frequency sweep using f(outer) as the frequency at which to commence the sweep. First, some calibration step may be performed (218). This calibration step may determine the frequency f(outer). This is a frequency at which stub pulses will reliably occur but which is not too far removed from a frequency at which stub pulses will disappear. This calibration step may further determine the incremental frequency change needed for this sweep. This frequency and/or the incremental value may be stored for use when performing tuning.

Next, the H-bridge circuit may be driven at the predetermined frequency f(outer) as well as a predetermined duty cycle so that stub pulses are detected (219). In one instance, the frequency is 39 KHz and the pulse width is 1000 ns. In this case, the duty cycle is about 3.9% if the pulse train that controls one of the H-bridge switch pairs is considered (e.g., either switch pair 150, 152 or switch pair 156, 158), is about 7.8% when the pulse trains for both switch pairs are taken into account.

The drive frequency is then adjusted until stub pulses first disappear at frequency f(disappear) (220). This incremental adjustment will entail an incremental frequency increase or incremental period decrease if f(outer) is below the resonant frequency of the system. Conversely, the incremental adjustment will involve an incremental frequency decrease or an incremental period increase if f(outer) is above the resonant frequency of the system. This incremental adjustment can use an increment value determined during the calibration process, in one example. As one example involving an increasing frequency sweep, the period may be decreased each step by about 46 ns. This will roughly correspond to a frequency increase during each step of the sweep of between 70 Hz and 92 Hz (with the frequency changes getting larger as the drive frequency gets higher).

Once stub pulses have disappeared, the incremental adjustments continue in the same direction (e.g., either increasing or decreasing frequency) until stub pulses first reappear at frequency f(reappear) (221). The final resonant drive frequency f(final), which approximates the resonant frequency of the system, may be set to the average of f(disappear) and f(reappear) (222). Finally, the duty cycle and/or voltage at which the H-bridge is being driven may be adjusted to predetermined values (223). In one example, these values may be set to predetermined "post-tuning" values, such as a voltage of 11 volts and a duty cycle of between 30%-40%. In another example, the duty cycle and voltage may remain set to their "tuning" values which in one embodiment is roughly 7.8% when the pulses driving both switches 150 and 156 are considered (or about 3.9% for the pulse train controlling either of switch 150 or 156).

Competing interests exist in determining whether to choose a final duty cycle that is larger or smaller. One the one hand, at a large duty cycle (e.g. between 20%-45%), stub pulses appear much more readily when the system is out of tune. In other words, the system is more "sensitized" to a divergence from the system resonant frequency such that this condition can be detected more quickly. Using a large duty cycle may also be more efficient when transferring power for reasons discussed above. On the other hand, when using a large duty cycle, the two stub pulse frequencies will be close to the nominal system frequency (e.g., the unloaded resonant frequency of the antenna 78) and the difference between these two stub pulse frequencies will not be very great. As a specific example, in reference to step 214 of FIG. 6A, the difference between f(stub1) and f(stub2) will not be large. Therefore, averaging these two frequencies will not be as meaningful or yield a resonant frequency that is as precise as if the two frequencies were farther apart.

Conversely, when the duty cycle is selected to be smaller (e.g., smaller than 20% for a single switch pair, or in one example, even smaller than 5% for a single switch pair), the two frequencies surrounding resonance at which the stub pulses first appear (e.g., f(stub1) and f(stub2) of FIG. 6A step 214) will be farther away from one another. As a result, taking the average of these frequencies to obtain the tuned resonant frequency will yield a more precise result. However, in this case, the system is not as sensitized to being out-of-tune. That is, the drive frequency can diverge further from resonance before stub pulses will appear, and the system may not detect as quickly that an out-of-tune condition exists. Therefore, the system may remain out of tune longer before re-tuning is initiated.

In view of the foregoing, in one example, it may be desirable to set the duty cycle to a smaller value to improve the accuracy during the tuning process. For instance, in one example, the duty cycle of the signal driving one switch pair is set to under 10%. In a still more particular example, this duty cycle is reduced to under 5%. After tuning has been completed, the duty cycle may be set to a larger value (e.g., over 30%) to sensitize the system for an out-of-tune condition and improve power transfer. Thereafter, when an out-of-tune condition exists using this larger duty cycle, the duty cycle may again be decreased to enhance tuning accuracy and so on.

The method of FIG. 6B may be performed very quickly if f(outer) and the frequency increment used for frequency adjustment are selected properly. The entire operation can, in one example, be performed in fewer than seventy increments. In one example, control circuit 88 operates at a frequency which allows this operation to be completed in less than one-tenth of a second, providing virtually real-time response.

Determining system resonant frequency according to methods described herein may be performed once when charging circuit 70 is first paired with patient 4. This will determine a system resonant frequency that takes into account such factors as patient body type, location and orientation of IMD 2, type of IMD 2, characteristics of secondary coil 56, typical spacing between primary coil 76 and secondary coil 56, and so on. Once this initial determination is made, the determined resonant frequency (e.g., f(final)) may be saved for use in all future recharge sessions. For instance, this frequency may be saved in storage device 90 of charging circuit 70, storage device 73 of external device 100, a storage device of IMD 2 or alternatively in some other storage device. Thereafter, all recharge sessions may be conducted at this frequency regardless of any measurements or indications made concerning recharge efficiency. In another example, this recorded frequency may be used as the nominal frequency (e.g., as in step 200 of FIG. 6A) the next time it is determined the frequency needs to be re-tuned.

In yet other examples, frequency may be calibrated each time a recharge session is initiated regardless of whether it has been done in the past. In another example, the resonant frequency may be re-determined at predetermined time increments throughout the recharge session (e.g., one minute.) In still other embodiments, a user may provide some type of input (e.g., selecting a frequency tuning option provided by a user interface) that initiates the tuning function.

In still other embodiments, a trigger event may initiate frequency re-tuning. For instance, in a system that utilizes telemetry communication between IMD 2 and charging circuit 70 and/or an additional external device such as external device 100 (FIG. 2), the IMD 2 may provide information indicative of the efficiency of the recharge session. Such information may include a measurement of current within, or voltage across, secondary coil 56, a current or voltage associated with rechargeable power source 50 of IMD 2 (e.g., a recharge current generated to rechargeable power source 50), a quantity of magnetic flux coupling secondary coil 56, or some other measure of the efficacy of the recharge session. When a change in one or more of these measurements indicates recharge efficiency may have decreased (e.g., when the current flowing to rechargeable power source 50 decreases below some threshold amount), charging circuit 70 may be prompted to determine whether stub pulses have appeared in the tank waveform, and if so, initiate frequency re-tuning according to any of the methods described above in reference to FIGS. 6A and 6B.

In yet another embodiment, the metric used to trigger frequency re-tuning may be temperature. For instance, temperature sensor 95 in antenna 78 and/or temperature sensor 51 in IMD 2 may be employed to determined temperature increases associated with antenna 78 or IMD 2 respectively. Such temperature increases may be an indication of power being lost as heat, and hence a less-than-optimal drive frequency. Any one of such temperature sensors may be used alone or in combination with other temperature sensors to trigger another search for the resonant system frequency according to any of the methods of FIGS. 6A and 6B or a variation thereof.

As previously discussed, the re-appearance of stub pulses may be used to trigger re-tuning in one embodiment. For instance, control circuit 88 may be interrupt driven or instead utilize polling to determine when stub pulses have re-appeared. In one interrupt-based embodiment, the ability to detect relative timing between pulses may be incorporated into edge detect circuit 160 such that this circuit may generate a different interrupt depending on whether frequency needs to be increased or decreased. Control circuit 88 may then respond accordingly, thereby providing a system that quickly responds in an appropriate manner to an indication that a frequency adjustment is needed. This is important in a system that, for example, includes a flexible coil that can be deformed relatively easily to conform to the shape of a patient's body. Flexing of the coil may change the resonant frequency of the system. Moreover, a patient's changes in body position and/or movement of primary coil 76 relative to secondary coil 56 may likewise change the system resonant frequency. Any one or more of these conditions may result in the need to re-initiate one or more of the steps of the process of FIGS. 6A and/or 6B periodically throughout the recharge session in any of the ways previously discussed.

When re-tuning during recharge, it may be desirable to use an abbreviated version of any of the methods of FIG. 6A or 6B. For instance, in the case of FIG. 6A, it may be desirable to reduce the current duty cycle somewhat and re-execute only steps 212-216 to arrive at an adjusted frequency rather than performing the entire method. Alternatively, it may be desirable to reduce the duty cycle and re-execute only steps 202-206. In either case, once the resonant frequency has been re-determined, it may be desirable to return the duty cycle to the large pre-tuning value, thereby sensitizing the system to being off-tuned, as discussed above.

In yet another embodiment, a quick search may be completed to re-tune frequency using the steps of method of FIG. 6B, which is particularly efficient if the frequency f(outer) and the increment frequency value have been properly calibrated. Many combinations are possible within the scope of the disclosure.

The foregoing discusses approaches for tuning frequency so that recharge may be performed efficiently. This tuning is generally performed while the antenna 78 is stationary relative to secondary coil 56. In fact, it may be desirable for antenna 78 to be positioned in the optimal location for performing recharge before the frequency search is initiated. The optimal location may be that location that will result in the largest current being delivered to rechargeable power source 50 at a given power level. The following discussion considers various approaches for performing this antenna location, as may be desirable prior to initiating the frequency search.

One way to determine optimal antenna location involves using telemetry module 59 of IMD 2 to communicate data to charging circuit 70 and/or an associated external device (e.g., external device 100). Such data may be indicative of the quality of coupling between primary coil 76 and secondary coil 56, wherein quality of coupling involves the amount of magnetic flux coupling primary coil 76 and secondary coil 56. Examples of data that indicate coupling quality include current within secondary coil 56, a voltage across the secondary coil, a current being delivered to rechargeable power source 50, a voltage associated with rechargeable power source 50, a quantity of magnetic flux coupling secondary coil 56 and so on. For instance, as the coupling quality increases, the current being delivered to rechargeable power source 50 will generally likewise increase. Thus, such information may be transmitted by telemetry module 59 to telemetry module 86 of charging circuit 70 and/or communication circuit 69 (FIG. 2) and thereafter used to provide feedback to a user. Such feedback may be provided via user interface 108 of external device 100 and/or a user interface of circuit module 110 (FIG. 3).

In one embodiment, signals indicative of coupling quality are translated into data that can be easily interpreted by the user to determine if and/or how to move antenna 78 to achieve better coupling. For instance, the amplitude of the current flowing into rechargeable power source 50 may be communicated to charging circuit 70 and translated into one or more bar indications on a user interface associated with charging circuit 70 or external device 100. Such a bar indication may be akin to the displays indicating reception quality of a cell phone. The user may continue re-positioning antenna 78 until the maximum number of "bars" is displayed. Other indications may be a number which increases as coupling quality increases, a color indicating coupling quality (red, yellow, or green), an audible indication that may provide verbal cues ("your getting closer") or a changing tone corresponding to coupling quality (e.g., getting higher or lower in pitch as coupling improves), and/or a tactile indication such as a vibration that changes frequency as the user approaches the optimal antenna location.

In yet some other embodiments, feedback may be provided via a user interface to identify a suggested direction of motion that may improve coupling. For instance, a sensor such as one or more accelerometers or gyroscopes may be carried by antenna and used to determine a current trend in motion of the antenna. That motion may be correlated with a trend in the change in coupling quality and used to suggest a new or continued direction of motion. Once the user has reached an optimal location for recharge, the system may provide feedback to indicate that the antenna 78 should now be maintained in the current position.

Alternatively or additionally, feedback may be provided concerning the speed of the movement of antenna. For instance, when it is determined that the optimal location for the antenna location is being approached, the user may be advised to slow speed of movement of the antenna so that the user will not "overshoot" the optimal location.

Many options are available for communicating feedback to a user, and the foregoing examples are merely several possible techniques that may allow a user to position antenna 78 to achieve at least an adequate coupling between primary and secondary coils. In any event, user interface 108 of external device 100, a user interface of circuit module 110, another user interface, or some combination thereof may be employed to provide the feedback to the user.

The above-described approach to locating the primary coil 76 with respect to the secondary coil 56 depends on the ability to transfer data from IMD 2 to an external device such as charging circuit 70 and/or external device 100. This, in turn, depends on rechargeable power source 50 having an adequate supply of power so that telemetry module 59 is operational.

In one example, rechargeable power source 50 is a so-called "zero-volt" battery capable of being discharged to 0, or substantially near 0, volts without negatively impacting the power source. In this type of an embodiment, it is possible that rechargeable power source 50 has been depleted so that telemetry module 59 is not operational to provide information that can be employed by a user to position primary coil 76 relative to secondary coil 56. In this case, some other mechanism is needed for this purpose.

According to one aspect, the frequency tuning mechanism described above may be used to locate an optimal, or at least an adequate, location for antenna 78 when communication cannot be established between telemetry module 59 of IMD 2 and an external device. In this example, some, or all, of the steps of the process of FIG. 6A or 6B may be executed as a user moves the antenna in the vicinity of secondary coil 56. The change in location will result in a corresponding change in the determined resonant frequency of the system. An optimal location will yield the largest resonant frequency.

To use a frequency tuning mechanism to locate an unresponsive device, the steps of FIG. 6A or 6B, or some subset thereof, must be completed fast enough so that a meaningful correlation can be drawn between a currently-reported system resonant frequency and the current location of antenna 78. Thus, when the tuning mechanism is used for location purposes, some streamlining of the process of FIG. 6A or 6B may be desirable. For instance, it may be desirable to use different starting points and increment values during the location process than are used for recharge frequency tuning. These alternative values may provide a "good enough" frequency determination relatively quickly (e.g., substantially in real-time) so that a reliable frequency indication can be provided as the antenna 78 location changes.

As a specific example, the process of FIG. 6A may utilize a larger duty cycle (e.g., 20% for a single switch pair) in step 200 than would otherwise be used when tuning for recharge. Additionally, the increments employed in steps 202 and 204 to increase and decrease frequency to locate the high-end and low-end frequency, f(high) and f(low), respectively, may be larger than would otherwise be employed in the recharge tuning context. Moreover, the average frequency f(ave) determined in step 206 may be considered a "good enough" surrogate for use in the location process such that the remaining steps of FIG. 6A are omitted. In such an embodiment, the process may continually repeat steps 200-206, reporting the determined f(ave) to the user as antenna 78 is re-located. This may allow a near real-time response to the movement.

As another example, steps 200-206 of FIG. 6A may be omitted, with a saved value for f(ave) being employed as a starting point, while repeating the processing of steps 208-214.

In one embodiment, the user may then be provided with data indicative of values of f(final) as the antenna is moved, with the location yielding the largest resonant frequency value being that location associated with optimal coupling between the primary coil 76 and secondary coil. This feedback may be provided substantially in real-time in one embodiment. Such feedback may be generated by control circuit 88 and/or control circuit 71 based on information associated with a resonant frequency value, and may be provided via user interface 108 and/or a similar user interface of recharge module 110 in one example.

Another example may simply utilize a stored value for f(final) as the starting point for the frequency-locator method. In this case, it is assumed that f(final) was previously determined for this charging circuit 70 and for patient 4 during a recharge session when IMD 2 may have had the capability to communicate with charging device and/or external device 100. The communication may allow an optimal recharge location to be determined via metrics that indicate coupling quality between the primary coil 76 and secondary coil 56, such as the amplitude of the charging current being supplied to rechargeable power source 50, a current or voltage in or across secondary coil 56, a current or voltage at some other location within a circuit of IMD 2, and so on. Since the frequency f(final) was previously established using a location known to be substantially optimal, this frequency can now be used to re-locate that optimal position. That is, H-bridge circuit 148 may be driven with the previously-recorded frequency for f(final). Antenna 78 may then be moved around the vicinity of secondary coil 56. During this movement, edge detect circuit 160 and control circuit 88 may monitor the existence and size of stub pulses in the monitored tank signal. The optimal location may be the position that does not result in any stub pulses at this drive frequency as identified by control circuit 88. In another embodiment, control circuit 71 may provide this location function. The processing required to complete this determination may be performed very quickly such that feedback is provided in near real-time.

In one embodiment, the user may be provided with feedback based on whether the stub pulses are widening or narrowing. For instance, if current movement is causing the pulses to widen, feedback may be provided indicating direction of movement should be reversed. Similarly, if the pulses are narrowing, some indication may be provided that the user is "homing in" on the optimal location. Many mechanisms and types of feedback are possible, as discussed above. This feedback may be provided substantially in real-time in one example so that the feedback has a meaningful correlation to a current position of antenna 78. The feedback may be generated by control circuit 88 and/or control circuit 71, which may provide an indicate based on the stub pulses that can be communicated to a user via a user interface, such as user interface 108 of external device 100 or a similar user interface of recharge module 110.

In yet another variation of the foregoing approach, a simple frequency sweep may be performed wherein the drive frequency for the H-bridge is continually varied around a selected "mid-point" frequency. This selected mid-point frequency is preferably one that is associated with resonance of the loaded system. For instance, the mid-point frequency may be a previously-determined frequency f(final) that is determined in any of the ways discussed above, or may instead be a known self-resonance frequency of charging circuit 70 and antenna 78 when the antenna is not loaded. Other selected mid-point frequencies may be used in the alternative. In any event, the drive frequency of H-bridge may be systematically varied around this mid-point frequency, starting below and ending above (or vice versa) that mid-point. While the frequency variation is occurring, control circuit 88 may be monitoring for stub pulses. The location at which the highest drive frequency occurs without generation of stub pulses may be identified by control circuit 88 and/or control circuit 71 as the optimal recharge location and this information may be conveyed to the user by employing feedback of any of the types described above.

Yet another example may continually perform a sweep from one side of the tuned region to the other in a manner described with respect to FIG. 6B. If frequency or period deltas are selected appropriately as determined during a calibration process, one sweep can be completed very quickly so that feedback as to resonant frequency can be provided in substantially real-time. As set forth about with respect to one particular embodiment, one sweep may require only about one-tenth of a second to complete. Thus, if the speed of the sweep is selected accordingly, the response time of the system is more than adequate to allow an optimum or near-optimum location to be identified.

In one embodiment, during a frequency-sweep location process, the resonant frequency of the system may be monitored until it is "close enough" to the known resonant frequency of the system at the optimal antenna location (e.g., f(final)). That is, the user need not continue to adjust antenna location until f(final) is actually achieved. Instead, the user need only find a location that that is known to correspond to at least some minimum acceptable level of coupling between the primary coil 76 and the secondary coil 56 (as will be indicated by some frequency previously associated with this "good enough" level of coupling). This may minimize user frustration as well as time spent re-positioning antenna 78 until the location associated with f(final) is actually achieved.

In some embodiments, "landmark" indications may be used as a starting point for positioning antenna 78 close to the location known to be optimal for recharge. Such landmark indications may involve visible indicators on the patient's body, such as scars, irregularities in skin pigmentation, or other visible physical attributes. According to one aspect, small tattoos which are barely visible, or perhaps not visible at all, to the naked eye, may be applied to the patient's skin to mark the position of antenna 78 for optimal recharge. Such landmarks may be detected by one or more optical sensors located in or around antenna 78 and used to re-position antenna.

As one example of the foregoing, the optimal recharge location may initially be determined by feedback available from IMD 2 via telemetry communication during a recharge session performed when rechargeable power source 50 has not been depleted. Once antenna 78 is positioned using this feedback, landmark information for this physical location (e.g., the pattern of any existing physical attributes) may be gathered (e.g., using sensors provided on antenna 78.) This landmark information may be stored in storage device 90 of charging circuit 70 or in another storage device. Thereafter, when antenna 78 is positioned in the vicinity of IMD 2, a landmark pattern for a current location of antenna 78 may be detected and compared to the recorded landmark pattern associated with the optimal recharge location. Pattern recognition algorithms may be employed to provide feedback to a user on how to move antenna 78 to center the antenna over the appropriate landmark pattern. This guidance can be provided without establishing telemetry communication with IMD 2. In one embodiment, after an approximate location is selected based on visual indicators, the location may be fine-tuned using any of the other location mechanisms described herein.

Figure 7:
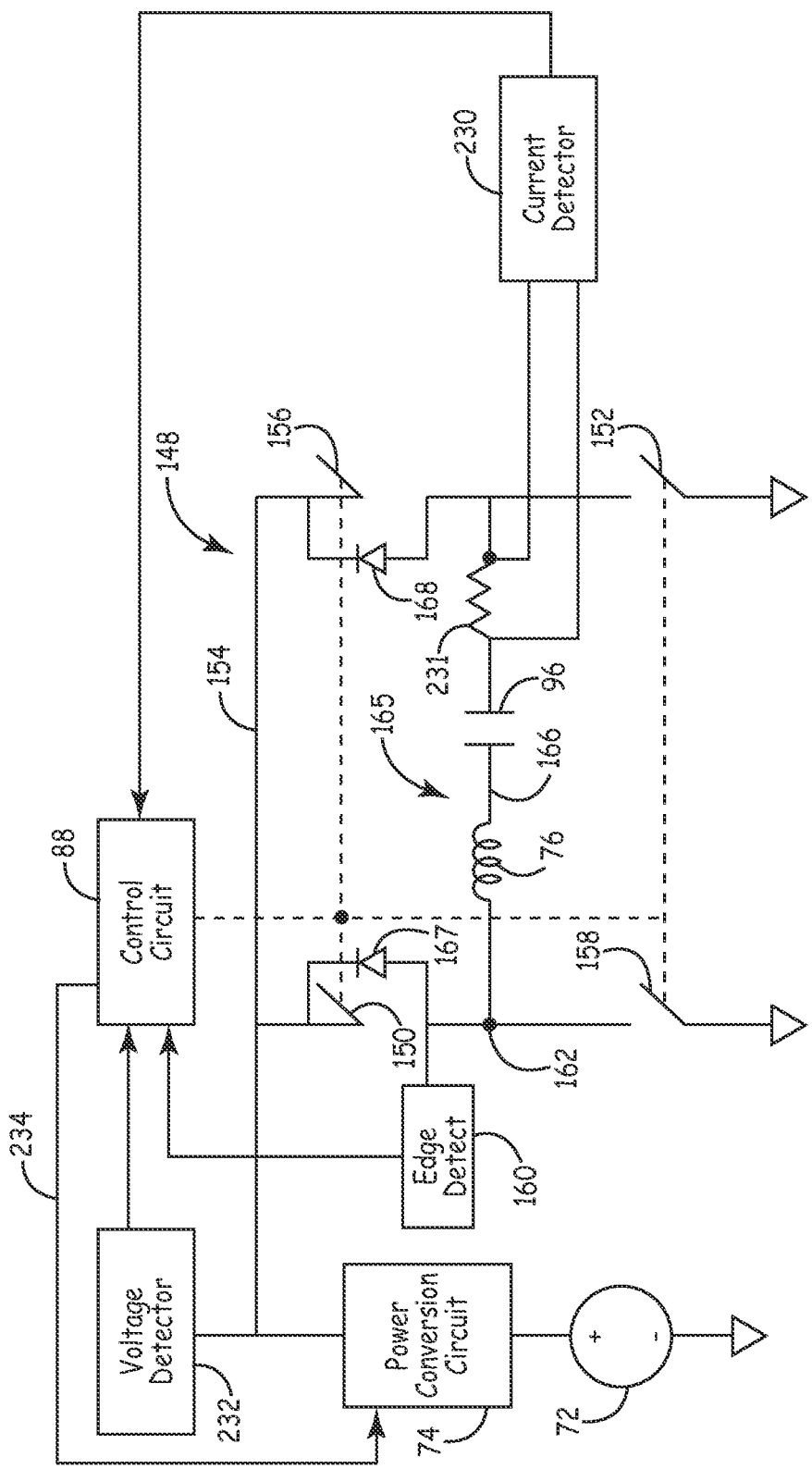
FIG. 7 is a circuit diagram similar to that shown in FIG. 4 that includes additional circuit elements for aiding in locating the antenna.

Still other mechanisms are available for performing antenna location as may be described in reference to FIG. 7. FIG. 7 is a circuit diagram similar to that shown in FIG. 4, with those elements that are similar to those shown in FIG. 4 being labeled with like numeric indicators. Unlike the embodiment of FIG. 4, the circuit of FIG. 7 includes a current detector 230 to sense the current through tank circuit 165 by measuring voltage across resistor 231.

In one embodiment, current detector 230 detects the peak current level through the tank circuit, but current detector 230 may measure a different current level in other embodiments (e.g., root-mean-square (RMS) current value, etc.) The monitored current level is provided to control circuit 88.

FIG. 7 also comprises a voltage detector 232. This voltage detector may monitor the voltage level being provided by power conversion circuit 74 at node 154. This voltage level is adjustable based on signal 234 provided by control circuit 88.

According to one embodiment of locating antenna 78, H-bridge circuit 148 is driven with a predetermined duty cycle and frequency. The frequency selected for this purpose may be a predetermined value of f(final), a self-resonance frequency of the system, or some other frequency. The antenna 78 is then swept over the vicinity of IMD 2. As the antenna approaches the optimal location for performing recharge, which is the location wherein coupling between the primary coil 76 and secondary coil 56 is greatest, the amount by which the secondary coil 56 loads the primary coil 76 increases to a maximum. This loading increases the AC series resistance of the primary coil 76, increasing the overall impedance of the tank circuit. Since the RMS voltage at node 154 is a product of the impedance of the tank circuit and the RMS current through the tank circuit, and assuming the voltage at node 154 is unchanging, the current in the tank circuit will be at a minimum where recharge coupling quality is at a maximum. Thus, control circuit 88 may monitor the current level of the tank circuit via current detector 230 for this minimum current level in the tank circuit to determine an optimal antenna location for recharge.

Using the foregoing current-based approach for locating an antenna, the power provided to the primary coil 76 will be at a minimum level when the optimal recharge location is found. This is because the power provided to the primary coil is directly related to both the RMS voltage of the tank circuit (which is constant) and the RMS current in the tank circuit (which is at a minimum at an optimal recharge location).

In view of the foregoing, instead of monitoring current for the location wherein current is at a minimum to determine optimal antenna location (i.e., a current-based locating approach), it may be desirable in some cases to use a voltage-based approach to locating antenna 78 when telemetry cannot be established with IMD 2. Using such an approach, the power level in primary coil 76 will be at a maximum (rather than a minimum) when the antenna is optimally located as follows.

According to one aspect of a voltage-based locating approach, control circuit 88 may drive tank circuit 165 at a predetermined frequency and duty cycle to achieve a predetermined current level through tank circuit 165. This predetermined frequency, duty cycle, and current level can be established during a calibration process, if desired, as will be discussed below. Then, as antenna 78 is re-positioned with respect to the general location of IMD 2, control circuit 88 adjusts the voltage being delivered by power conversion circuit 74 to maintain this predetermined current level in tank circuit 165. As a result of this voltage adjustment, voltage will incrementally increase as antenna 78 is moved closer to the optimal location for performing recharge, since at this optimal location, loading will also increase. The maximum voltage will be obtained at the optimal recharge location, as may be determined by control circuit 88. Using this voltage-based locating approach, a maximum power level will be transferred to primary coil 76 when antenna 78 is positioned at the optimal recharge location. This is opposed to a minimum power level that will be transferred when a current-based approach is employed.

In one alternative embodiment, during a voltage-based location process, voltage at node 154 need only attain a "good enough" voltage before the location is considered adequate to initiate recharge. In other words, rather than forcing the user to find the very best spot resulting in the absolute maximum voltage level possible, the user need only find a location that yields an acceptable voltage that is known to correspond to an acceptable power level in primary coil 76. This may minimize user frustration as well as time spent re-positioning antenna 78.

As described above, values used during a voltage-based location method may be calibrated to a given implant scenario. Such calibration may be performed during a recharge session wherein telemetry communication can be established with IMD 2. As one example, an optimal recharge position may be determined by finding the location at which an optimal level of coupling may be obtained between the primary coil 76 and secondary coil 56. At such a location, substantially the maximum current may be delivered to rechargeable power source 50, as reported by telemetry communication. Other metrics may be used in addition to, or instead of, current to find this optimal location at which coupling between the coils is likewise optimal, as discussed above.

Once this optimal location is determined when telemetry communication with IMD 2 can be established, control circuit 88 may tune the frequency at which the H-bridge circuit 148 is driven as discussed above. Next, control circuit 88 may adjust the power level delivered to tank circuit 165 such that substantially a predetermined recharge current is supplied to rechargeable power source 50. This power level may be adjusted by changing the duty cycle of the drive signal and/or the voltage being delivered to node 154. The power level needed to obtain a predetermined recharge current will vary based on implant depth and orientation, body type, etc. The tuned drive frequency, the final duty cycle, the current level through the tank circuit 165, and the voltage at node 154 may then be recorded as calibration data for the antenna location techniques.

Yet other calibration data may include a minimum acceptable voltage that is indicative of a "close enough" antenna position. At such a location the minimum acceptable level of coupling may exist between the primary coil 76 and the secondary coil 56 to obtain a reasonable flow of current in rechargeable power source 50. This "close enough" location may be determined for instance, by moving antenna 78 away from the known optimal location to a location wherein the current flowing into rechargeable power source 50 drops to some level considered to be the minimum level needed to sustain a recharge session. For instance, this may be the location wherein the current flowing into rechargeable power source 50 drops to 30% of the maximum level. The voltage at node 154 may be adjusted to obtain the current value through tank circuit 165 that was recorded when the antenna 78 was in the optimal recharge location. This adjusted voltage level may be recorded as the level corresponding to the minimal acceptable level of coupling between the primary and secondary coils that will provide at least an adequate flow of current to rechargeable power source 50. When at least this voltage level is obtained during an antenna location process, it may be ascertained that the antenna position is "close enough" to the optimal position to initiate recharge.

The foregoing, and other, calibration data may be recorded during a recharge session when telemetry feedback is available. This data is then available for use in locating antenna 78 when telemetry is unavailable to aid in this process. Use of the calibration data makes the process more accurate and efficient, since levels within the tank circuit 165 will be tuned to an implant scenario of a particular patient.

Figure 8:
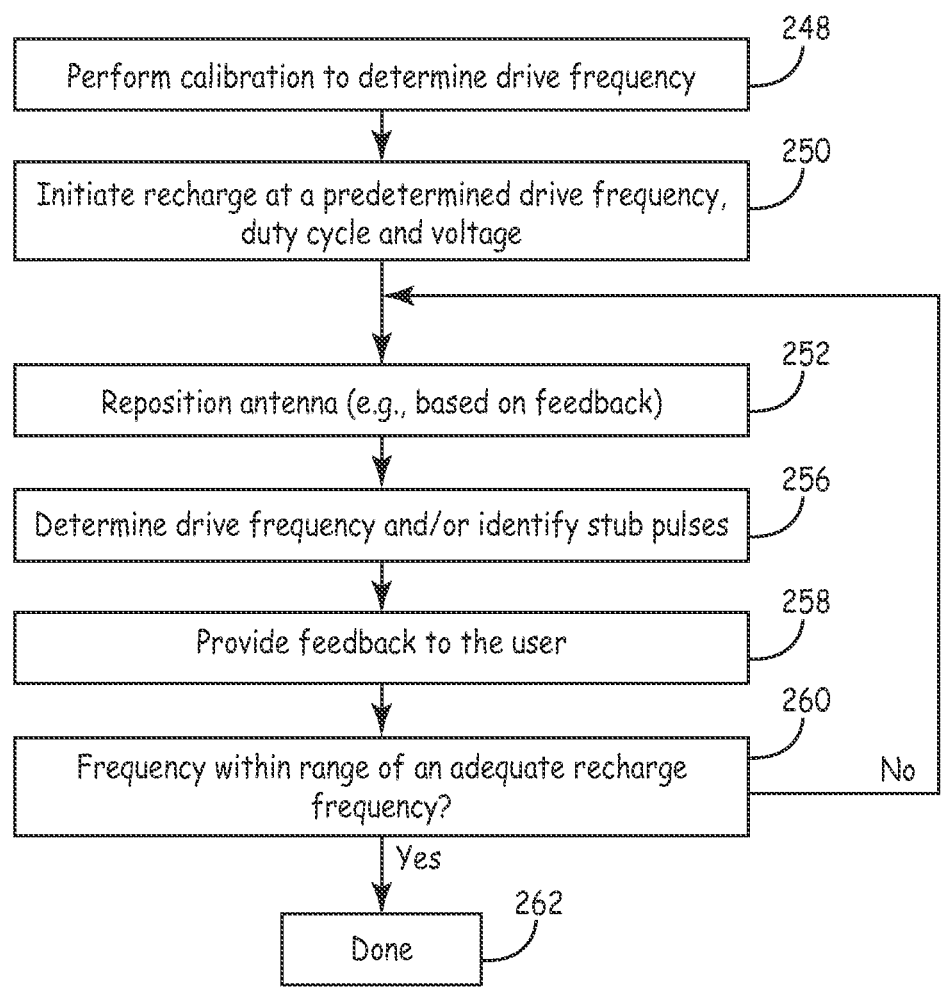
FIG. 8 is a flow diagram illustrating one method of positioning an antenna by altering drive frequency of a charging circuit.

FIG. 8 is a flow diagram illustrating one method of positioning antenna 78 by altering drive frequency of the recharger. In one example, calibration may be performed when communication with IMD 2 is established to determine the system resonant frequency that will be achieved at the optimal recharge location (248).

Recharge may be initiated at a predetermined drive frequency, duty cycle and voltage (250). In one example, the predetermined drive frequency may be the frequency determined in step 248.

Antenna 78 (and hence primary coil 76) may be positioned relative to IMD 2 (252). Such positioning may involve moving antenna in a sweeping motion relatively slowly over an area in proximity to IMD 2. While the antenna is being re-position in this manner, a resonant frequency for a current location of antenna may be determined in one example or the appearance of stub pulses may be identified in another example (256). In the former example, the resonant frequency may be determined using any of the mechanisms discussed above, include using all, or some subset of the steps discussed in regards to FIG. 6A and/or FIG. 6B. According to one simple approach of determining frequency, at each location, frequency is incrementally adjusted around a selected mid-point frequency to determine a frequency wherein no stub pulses are detected by edge detect circuit 160. This will approximate the resonant frequency for this location. The resonant frequency will become closer to that recorded in the calibration step 248 as antenna is moved closer to the optimal location. Alternatively, if the locating process was initiated at a known system resonant frequency that was determined during calibration step 248 to be the resonant frequency at the optimal recharge location, step 256 may instead involve determining if stub pulses have disappeared at this location. Stub pulses will become more narrow, and eventually disappear altogether, as the optimal location is approached.

In either case, feedback may be provided to the user (258). Feedback may be provided based on the resonant frequency that is determined for each location and/or the width and/or occurrence of stub pulses at a given location. This feedback may indicate how the quality of recharge coupling is changing as antenna 78 is moved. Feedback may suggest a direction in which, or a speed at which, the user may move antenna 78 to improve the quality of recharge coupling.

In one example, a determination of resonant frequencies and/or identification of stub pulses may occur in real-time or near real-time so that feedback may be provided while antenna 78 is still located over a position corresponding to that frequency. Many mechanisms are available to provide this feedback, as discussed above.

The process may be continued until a location has been reached that will provide optimal, or at least adequate, recharge coupling (260). For instance, this location may be one wherein the resonant frequency at this location is within some predetermined percentage of the resonant frequency occurring when antenna 78 is in the optimal position for recharge (e.g., f(final)). When the frequency is within this range, the coupling quality is at least adequate. In one example, "adequate recharge coupling" may be defined as coupling that results in enough magnetic flux coupling primary and secondary coils so that at least some minimum power level is available to recharge the rechargeable power source 50. This may be determined by measuring current or voltage provided to the rechargeable power source 50.

When a frequency meeting the predetermined criteria has been met, the location process may be considered complete (262). Otherwise, processing may return to step 252, wherein re-positioning of antenna 78 continues and resonant frequency is re-determined. In one embodiment, if no location is found that yields a resonant frequency meeting the criteria of step 258 within a predetermined time period, some intervention may be provided. This is discussed further with respect to FIG. 11 below.

Figure 9:
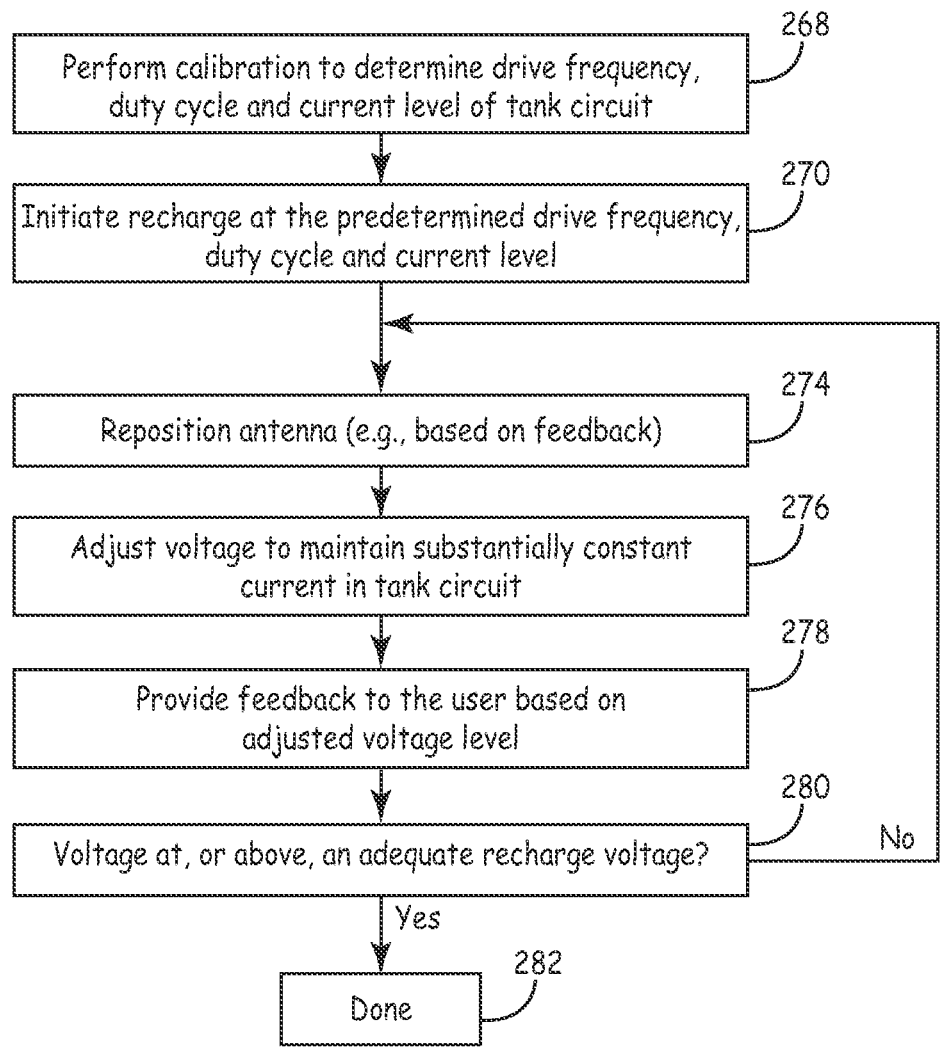
FIG. 9 is a flow diagram illustrating one method of positioning an antenna by altering a voltage of a charging circuit.

FIG. 9 is a flow diagram illustrating one method of positioning antenna 78 by altering a voltage of the recharger. In this scenario, a calibration step may be performed when telemetry communication is available to determine an optimal recharge location. This calibration step may determine an H-bridge drive signal (e.g., including duty cycle and frequency) at which to drive the H-bridge circuit and/or voltage to supply to the H-bridge in order to achieve some desired level of recharge current being supplied to rechargeable power source 50. When this desired level of recharge current is obtained within IMD 2, the current in tank circuit 165 may be recorded, along with the duty cycle and frequency of the H-bridge drive signal. The voltage at node 154 may also be recorded at the optimal location and/or at one or more other locations (e.g., at locations wherein the current to rechargeable power source 50 has dropped to some predetermined level(s)), if desired. This calibration data will provide the predetermined current level, duty cycle, and frequency that will be maintained constant during the voltage-based location process (268).

Next, recharge may be initiated at the predetermined drive frequency and duty cycle, with the voltage of the H-bridge circuit being adjusted to obtain the predetermined current level in the tank circuit, as determined by the calibration data (270). Antenna may be positioned (or re-positioned) relative to IMD 2 (274). The current in tank circuit 165 may have changed because of the antenna movement. Therefore, control circuit 88 may adjust voltage at node 154 to maintain a substantially constant current in the tank circuit 165, which in one embodiment is the current level recorded during the calibration step (276). During the re-positioning process, feedback may be provided based on the voltage that is determined for each location. This feedback may indicate how the quality of recharge coupling is changing as antenna 78 is moved (278). In one example, the voltage may be determined in real-time or near real-time so feedback is provided while antenna 78 is located over a corresponding position. Recall that voltage will increase as the optimal recharge location is approached, since loading increases to a maximum at the optimal position.

In one embodiment, feedback may suggest a direction in which, or a speed at which, the user may move antenna 78 to improve the quality of recharge coupling. Many mechanisms are available to provide this feedback, as discussed above.

Voltage may be monitored to determine when a location has been reached that will provide at least adequate recharge coupling (280). In one embodiment, this location may be one wherein the voltage is above some predetermined minimum acceptable voltage known to be present when antenna 78 is located within "good enough" proximity of secondary coil 56 to conduct adequate recharge. In another example, this location may be one wherein the voltage is within some predetermined percentage of the known maximum voltage that would occur at the optimal recharge location. As previously described, both the minimum acceptable voltage as well as the maximum voltage may be recorded during calibration.

When a voltage meeting the predetermined criteria has been met (e.g., the voltage is within a predetermined percentage of maximum voltage), the locating process may be considered complete (282). Otherwise, processing may return to step 272, wherein re-positioning of antenna 78 continues (as may be based on the provided feedback) and voltage is re-determined. In one embodiment, if no location is found that yields a voltage meeting the criteria of step 278 within a predetermined time period, some intervention may be provided. This is discussed further with respect to FIG. 10 below.

The foregoing voltage-based techniques provide examples of a system for finding one or more locations at which a primary coil of a charging device may be placed with respect to a secondary coil of an implantable medical device to achieve at least a minimum level of coupling between the primary coil and the secondary coil. That minimum level of coupling will provide at least adequate recharge of rechargeable power source 50. As described above, this system may include a tank circuit comprising the primary coil. A control circuit is configured to monitor a first signal associated with the tank circuit while the location of the primary coil is changing, and further to automatically adjust a second signal associated with the tank circuit to maintain the first signal at a substantially constant level while the location of the primary coil is changing. Feedback is provided to a user based on the second signal. Adjusting the second signal may increase a level of power supplied to the tank circuit as the primary coil is moved closer to any of the one or more locations. In some examples, the first signal may be a current in the primary coil, and the second signal may be a voltage at which the primary coil is being driven. In one instance, the feedback may be provided in real time so that feedback has a meaningful correlation to a current position of the antenna 78.

Such voltage-based location techniques further include a method for finding one or more locations at which a primary coil 76 of a charging device may be placed with respect to a secondary coil 56 of an implantable medical device 2 to achieve at least a minimum level of coupling between the primary and the secondary coils. This method may comprise monitoring a first signal (e.g., a current) associated with the primary coil of the charging device while a location of the primary coil is changing with respect to the IMD. A second signal (e.g., a voltage) associated with the primary coil may be automatically adjusted to maintain the first signal at a substantially constant level while the location of the primary coil is changing. Adjusting the second signal may increase a level of power supplied to the tank circuit as the primary coil is moved closer to any of the one or more locations. User feedback may be provided based on the second signal.

Other examples of these approaches include a method of locating a primary coil 76 of an external recharger relative to a secondary coil 56 of an implantable medical device 2. According this method, a tank circuit 165 of an external recharger may be driven while repositioning the primary coil 76 relative to the secondary coil 56. A first signal associated with the tank circuit 165 may be maintained at a constant level by adjusting a second signal associated with the tank circuit while the primary coil is re-positioned. The second signal may be monitored to determine a position of the secondary coil that achieves at least adequate coupling between the primary coil and the secondary coil.

If desired, frequency-based and voltage-based location approaches may be used in tandem to find an antenna position for recharge. For instance, once an approximate location is obtained using a voltage-based method as discussed above, a frequency-based approach may be used to fine-tune the location. Any of the methods discussed above with respect to stub-pulse detection may be used for this purpose. For instance, once antenna 78 has been positioned at an approximate location, H-bridge circuit 148 may be driven at a previously-determined frequency of f(final) to confirm that no stub pulses appear within the tank signal. If stub pulses do appear, it may be desirable to fine-tune the location. Alternatively, a frequency-based approach may be used to determine an approximate location, and a voltage-based approach can then be used to confirm that a maximum voltage is indeed present at that location. The maximum voltage used for this purpose may have been previously recorded as part of the calibration data.

The above description provides several examples of locating primary coil 76 in a near-optimal, or at least adequate, position for recharge. Some of these location techniques may be used when IMD 2 is not able to communicate with charging circuit 70 or another device such as external device 100. As previously discussed, once primary coil 76 has been located in at least an adequate position to conduct recharge, frequency tuning may optionally be performed to determine a frequency that is optimal or near-optimal for performing recharge at that location. Recharge may then be initiated.

Another aspect of this disclosure relates to not only tuning frequency, as may be performed before, and/or during recharge, but also to tuning the power being delivered to primary coil 76 during recharge. Control of this power may be necessary to control heat dissipation by antenna 78 and IMD 2 so that regulatory limits and patient preferences are not exceeded.

The amount of heat being dissipated within IMD 2 and antenna 78, and thus the need to limit power in primary coil 76, may be determined in a number of ways. One direct method involves measuring temperature of IMD 2 by one or more temperature sensors 51 in the IMD. For instance, a temperature of IMD 2 may be reported via telemetry communication to charging circuit 70. Likewise, temperature sensor 95 may be used to determine when temperature of antenna 78 is exceeding a predetermined maximum. In either case, the heat dissipation limits for IMD 2 and/or antenna 78 may be dictated by regulatory requirements, manufacturer limits, patient preferences, and/or other considerations.

In either case, if a temperature reaches a predetermined maximum temperature (such as 41° C.), control circuit 88 may first re-tune frequency to ensure the system is being driven at resonant frequency. Control circuit 88 may then reduce power being delivered to tank circuit 165, which can be accomplished by decreasing the drive signal duty cycle and/or H-bridge voltage.

While temperature sensors (e.g., sensors 51 and 95) may provide a way to directly measure heat dissipation during recharge, temperature sensors may not be available in all systems. Therefore, according to another aspect, heat dissipation in antenna 78 and IMD 2 may be calculated rather than measured, as follows.

It is known that of the total power that is supplied to the primary coil, referred to as "Power_Primary", at least some of this power, or "Power_Charge", will be used to recharge power source 50 of IMD 2. Some power will be lost to heat that is dissipated in the primary coil, referred to as "Heat_Primary". The rest of the power is lost as heat in the IMD 2, or "Heat_IMD". Thus, the amount of power lost as heat in the IMD may be calculated as follows:

$$\text{Heat\_IMD} = \text{Power\_Primary} - \text{Heat\_Primary} - \text{Power\_Charge} \quad \text{(Equation 1)}$$

Assuming both the voltage and current in primary coil 76 are sine waves, the value for Power_Primary is the product of the RMS current in the primary coil, the RMS voltage across the primary coil, and the cosine of the phase difference between these two signals. The RMS current in the primary coil may be determined directly by dividing the peak current in the coil, which is measured by current detector 230, by the square root of two. The RMS voltage across the primary coil is a function of the voltage at node 154, as may be measured by voltage detector 232, or may simply be a "known" value based on a setting of power conversion circuit 74. The frequency and duty cycle of the H-bridge drive signal are likewise "known" values available to control circuit 88, since control circuit 88 is controlling the drive signal. Finally, in one example, the RMS voltage in the primary coil may be determined as follows:

$$Vrms = \text{Voltage} \sqrt{\frac{2W}{1/freq}} \quad \text{(Equation 2)}$$

In this equation, "Voltage" is the voltage at node 154 provided by power conversion circuit 74, "W" is the width of a pulse driving either switch 150 or 156 (e.g., width of pulse 187 in FIG. 5B), and "freq" is the drive frequency of the H-bridge (e.g., the inverse of period "T" in FIG. 5B). Finally, in one example, it may be assumed that after frequency tuning has been performed, the phase difference between RMS current and RMS voltage is zero. Thus, using these relationships, the power being delivered to primary coil 76 can be determined using known and measured values.

While in one embodiment, the power delivered to the primary coil 76 assumes an in-phase relationship between current and voltage of the tank circuit 165 such that the phase difference is "zero", in another example, the phase difference may instead be measured to achieve more accuracy. This can be accomplished by comparing the timing of a signal at node 162 of the H-bridge circuit, as may be determined by edge detect circuit 160, to a zero crossing of the tank current waveform as indicated by current detector 230. To increase accuracy of this phase difference determination, calibration may be performed to ensure that delay imposed by edge detect circuit 160 is substantially the same as delay imposed by current detector 230. By determining the phase difference between RMS current and RMS voltage of the tank circuit 165, the power delivered to the primary coil (Power_Primary) 76 may be determined more accurately in cases wherein a phase difference is something other than zero.

The value for Heat_Primary is the product of the square of the RMS current in the primary coil (as determined by current detector 230) and a known system constant value for the AC series resistance of primary coil 76 itself at the nominal resonant frequency, which in this example is 41 KHz (absent of any contribution from loading because of coupling between the primary and secondary coils). This AC series resistance is a constant value that may be empirically determined or calculated, for instance. Control circuit 88 of one embodiment ensures that Heat_Primary does not exceed patient preference and/or regulatory limits by ensuring that the RMS current in the primary coil 76 does not exceed some predetermined maximum value.

The amount of power delivered to charge rechargeable power source 50 of IMD 2, or Power_Charge, may be determined as a product of the voltage delivered to rechargeable power source 50 and the recharge current for this power source, both of which may be measured in one embodiment and provided via telemetry module 56 to charging circuit 70.

In view of the foregoing, the values for Power_Primary, Heat_Primary, and Power_Charge may be used to determine the amount of power dissipated as heat (Heat_IMD) in IMD 2. In one embodiment, control circuit 88 may then adjust power delivered to primary coil 76 (Power_Primary) accordingly as discussed above, adjusting H-bridge voltage and/or duty cycle of the H-bridge drive circuit so that heat dissipation does not exceed regulatory requirements and patient comfort levels.

Some or all of the processing steps used to determine Heat_IMD may be performed by control circuit 88. In another embodiment, some of all of the processing steps may be performed by control circuit 71 of external device 100. In particular, external device 100 may be a patient programmer that communicates via telemetry circuit 69 with IMD 2 during recharge to receive current and voltage information so that a value for Power_Charge may be calculated. External device 100 may further receive via interface 84*a* information concerning the current, in the primary coil 76. Such information may enable control circuit 71 of external device to determine the heat being dissipated in the primary coil 76, or Heat_Primary.

In one embodiment, at any given time, external device 100 stores a value of the current power level being supplied to primary coil 76, or Power_Primary. As previously discussed, this can be determined based on the current and voltage levels in tank circuit 165 and the phase difference between these two signals. Based on the calculated values of Power_Charge and Heat_Primary, as well as the known value for Power_Primary, the current level for Heat_IMD may be determined. External device 100 may then determine whether either of the values of Heat_Primary or Heat_IMD has exceeded acceptable limits. If so, external device 100 may provide an indication to charging circuit 70 to decrease the power level in the primary coil 76 by some determined amount. The external device 100 will then update the stored value for Power_Primary. In this manner, external device 100 may control power being delivered to primary coil 76.

In one example, Power_Primary is maintained at a level such that the limiting one of Heat_Primary and Heat_IMD is just under desired limits. This will allow recharge to complete as quickly as possible. Thus, after determining values for Heat_Primary and Heat_IMD in any of the aforementioned ways, and if both are below acceptable limits, it may be desirable to increase Power_Primary so that the limiting one of these two values will be increased to just below limits. Thus, external device 100 of one example may provide an indication to charging circuit 70 to increase the power in the primary coil by some determined amount.

The foregoing embodiment "off-loads" some of the processing steps from charging circuit 70 to control circuit 71 of external device 100. In another embodiment, the processing steps could be partitioned in a different way. For instance, all or fewer processing steps could be performed by charging circuit 70. In some embodiments, for instance, external device 100 is not necessary for performing power adjustment at all such that all steps are performed by charging circuit 70.

When charging circuit 70 either receives an indication that a power adjustment is needed (e.g., from external device 100) or alternatively determines this adjustment is necessary, there are several ways to adjust the power in primary coil 76. In particular, charging circuit 70 may alter voltage at node 154 and/or duty cycle of the drive signal. In one example, Power_Primary is more sensitive to a change in duty cycle than a change in voltage. Thus, when a power change is needed, control circuit 88 may first adjust the duty cycle. In one embodiment, the adjustment will be limited such that the final duty cycle is within low and high limits. In one embodiment, the pulse of a pulse train driving either of switches 150 and 156 must be between 1000 ns and 6000 ns. This is between about 4% and 26% for the signal driving switch 150 or 156, or double these values if both switches 150, 156 are taken into account. Other duty cycle limits can be used in the alternative, keeping in mind that for a single one of switches 150 or 156, the duty cycle must be something under 50% to take into account the dead period. If the degree of power adjustment that is needed cannot be achieved by adjusting the duty cycle within these limits, control circuit may then further adjust voltage at node 154.

In one example, after charging circuit 70 either determines a level by which power may be adjusted, or alternatively receives the level of adjustment from external device 100, charging circuit 70 utilizes tuning data 90*b* (FIG. 2), which may comprise one or more look-up tables, to determine how to achieve this adjustment. In one example, the current frequency of the drive signal and the amount of the adjustment that is required may be provided as input to the look-up table to determine an amount by which to alter duty cycle and/or voltage at node 154. Such an embodiment may assume that the voltage and current in the primary coil 76 are in phase with one another. In another case, information concerning the phase difference between these two signals, as may be determined in a manner described above, may be provided as an additional input to the lookup table. In still another example, tuning data 90*b* may comprise equations instead of lookup tables to determine the changes needed to the duty cycle and/or H-bridge voltage. Such equations may be based on modeling of the H-bridge circuit, for instance.

In view of the foregoing, it will be appreciated that after frequency tuning of H-bridge circuit has been completed to achieve a current and voltage within primary coil 76 that are substantially in-phase, control circuit 71 and/or control circuit 88 may, in examples, select a duty cycle and/or voltage level that limit heat dissipation. This selection may be based on tuning data 90*b*, which may be stored within storage devices 90 of charging circuit 70, within storage devices 73 of external device 100, and/or within some other storage devices.

Tuning of power in the primary coil 76 (Power_Primary) may be performed at various time intervals. In one example, tuning of power may occur whenever frequency tuning occurs. In another example, tuning of the power in the primary coil 76 may be performed more often than tuning of the frequency. For instance, re-tuning of the frequency may occur only after a trigger event occurs, such as the appearance of stub pulses within a waveform of tank circuit 148. In contrast, re-tuning of Power_Primary may be performed at regular time intervals during recharge, such as once per minute.

Figure 10:
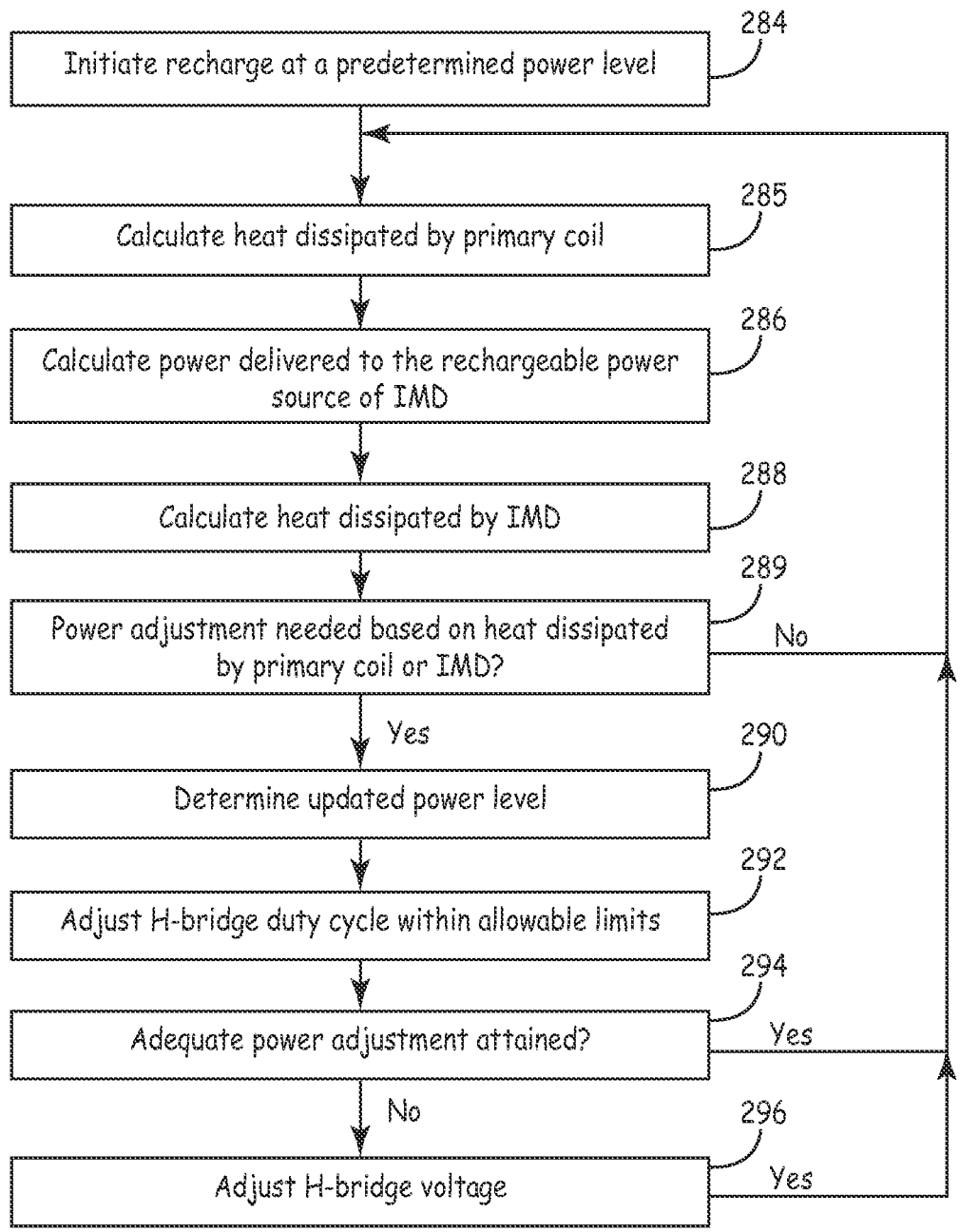
FIG. 10 is a flow diagram of tuning power in the primary coil according to one example method.

FIG. 10 is a flow diagram of tuning power in the primary coil according to one example method. First, recharge may be initiated at a predetermined power level (284). This power level may be an initial power level known to provide at least some minimum level of recharge current to rechargeable power source 50 when something other than optimal positioning has been achieved for antenna 78.

As discussed above, the power level in primary coil 76 can be controlled by adjusting duty cycle of the H-bridge drive signal and/or voltage of the H-bridge circuit. In one example, the initial power level may be associated with a predetermined duty cycle and voltage level. That is, an initial duty cycle and voltage level may be selected for use in initiating recharge after frequency tuning has been completed. This may be stored as calibration data 90*a* (FIG. 2) if desired, or recorded in some other manner.

Next, heat dissipated by the primary coil may be determined (285). In one instance, this is determined as the product of the square of the RMS current through the primary coil 76 and the resistance of primary coil 76. The RMS current may be measured in one embodiment and the AC series resistance of the coil is a known value that depends on the design of the coil. In one embodiment, the coil AC series resistance can be determined empirically or through known circuit modeling techniques.

The power delivered to the rechargeable power source of IMD 2 may also be determined (286). In one embodiment, this is determined as the product of the voltage of rechargeable power source 50 and the current being delivered to this power source. Both of these values may be measured by circuitry within IMD 2 and provided via telemetry to charging circuit 70 and/or to external device 100.

The heat dissipated by IMD may next be determined (288). In one example, the heat is determined by subtracting the heat dissipated by the primary coil and the power delivered to rechargeable power source as determined in steps 285 and 286, respectively, from the power being delivered to the primary coil, which is a known value.

Next, it is determined whether a power adjustment is needed based on the heat being dissipated by the primary coil 76 (as determined in step 285) or the heat dissipated by the IMD 2 (determined in step 289). Some maximum amount of heat dissipation may, in one case, be associated with each of the primary coil and IMD 2 such that if either the heat dissipation of the primary coil 76 or the IMD 2 exceeds the associated maximum amount, power delivered to the primary coil 76 is reduced. Otherwise, if heat dissipation for both IMD 2 and primary coil 76 is below limits, it may be desirable to increase the power level so that recharge completes more quickly. If neither of these conditions exists, power level may remain the same.

If no power adjustment is needed, execution may return to step 285 so that the process may be repeated. Otherwise, an updated power level for use in driving the primary coil 76 may be determined (290). The new power level may be determined by the amount the limiting one of the IMD heat dissipation or the antenna heat dissipation is above or below the target value. That is, the amount of the adjustment may be proportional to how far away the heat dissipation value is from the target value. In another embodiment, the amount of the adjustment may be some fixed amount that is applied regardless of how far away the heat dissipation value is from the target value. In any event, the updated power level may be saved for use in determining heat dissipated by IMD 2 in step 288.

Next, the power may be adjusted by the determined amount. As previously discussed, the adjustment to the power level can be performed by adjusting the H-bridge duty cycle (292). In one embodiment, this adjustment is made within predetermined allowable limits. For instance, the duty cycle for one switch pair cannot exceed about 26% although other values may be used in the alternative. It may further be desirable to set a lower limit such as about 4% for the duty cycle of one switch pair. Any limits may be selected for this purpose so long as the duty cycle for one switch pair is less than 50% by some amount needed to accommodate the dead period. In one example, one or more lookup tables may be used to map the desired power adjustment to a duty cycle adjustment. This determination may take into account the current duty cycle and the current frequency. In another example, instead of lookup tables, equations based on a circuit model may be used for determining an amount to alter duty cycle.

If the entire power adjustment cannot be achieved solely through a duty cycle adjustment in step 292 (294), the voltage level of the H-bridge circuit may be adjusted to bring the power level of primary coil 76 to the desired value (296). Again, the portion of the power adjustment that could not be accomplished through duty cycle modification may be mapped to a voltage adjustment by using one or more lookup tables. Alternatively, equations that model the circuit may be used for this purpose. Processing may then return to step 285 to repeat the process.

While the foregoing approach uses a duty cycle adjustment as the primary means for controlling power in primary coil 76, in another example, a power adjustment may be made by first adjusting voltage of the H-bridge circuit. Only if this is not sufficient will duty cycle then be adjusted. In another embodiment, adjustments may be made to both duty cycle and voltage to achieve a given level of power adjustment.

Power adjustment in primary coil 76 may be performed repeatedly throughout a recharge session, as shown in FIG. 10. Alternatively, steps of FIG. 10 may be performed at regular intervals, such as once per minute. In yet another example, execution of the process may be performed upon occurrence of a trigger event. For instance, when telemetry communication from IMD 2 indicates a significant change has occurred to the power being delivered to rechargeable power source 50, the process of FIG. 10 may be performed to adjust power to primary coil 76.

As previously discussed, the steps of FIG. 10 may be performed by control circuit 88, by control circuit 71 of external device, or by some combination thereof. In one example, most of the processing steps may be off-loaded to external device 100, which determines an amount of power level adjustment. This amount may then be communicated to charging circuit 70, which then converts the power adjustment into an appropriate duty cycle and/or voltage adjustment. In another embodiment, all steps may be performed by external device 100, which merely communicates the target voltage level and duty cycle to control circuit 88, which then affects the changes. These steps may be performed using hardware circuitry, programmed instructions, or any combination thereof.

Figure 11:
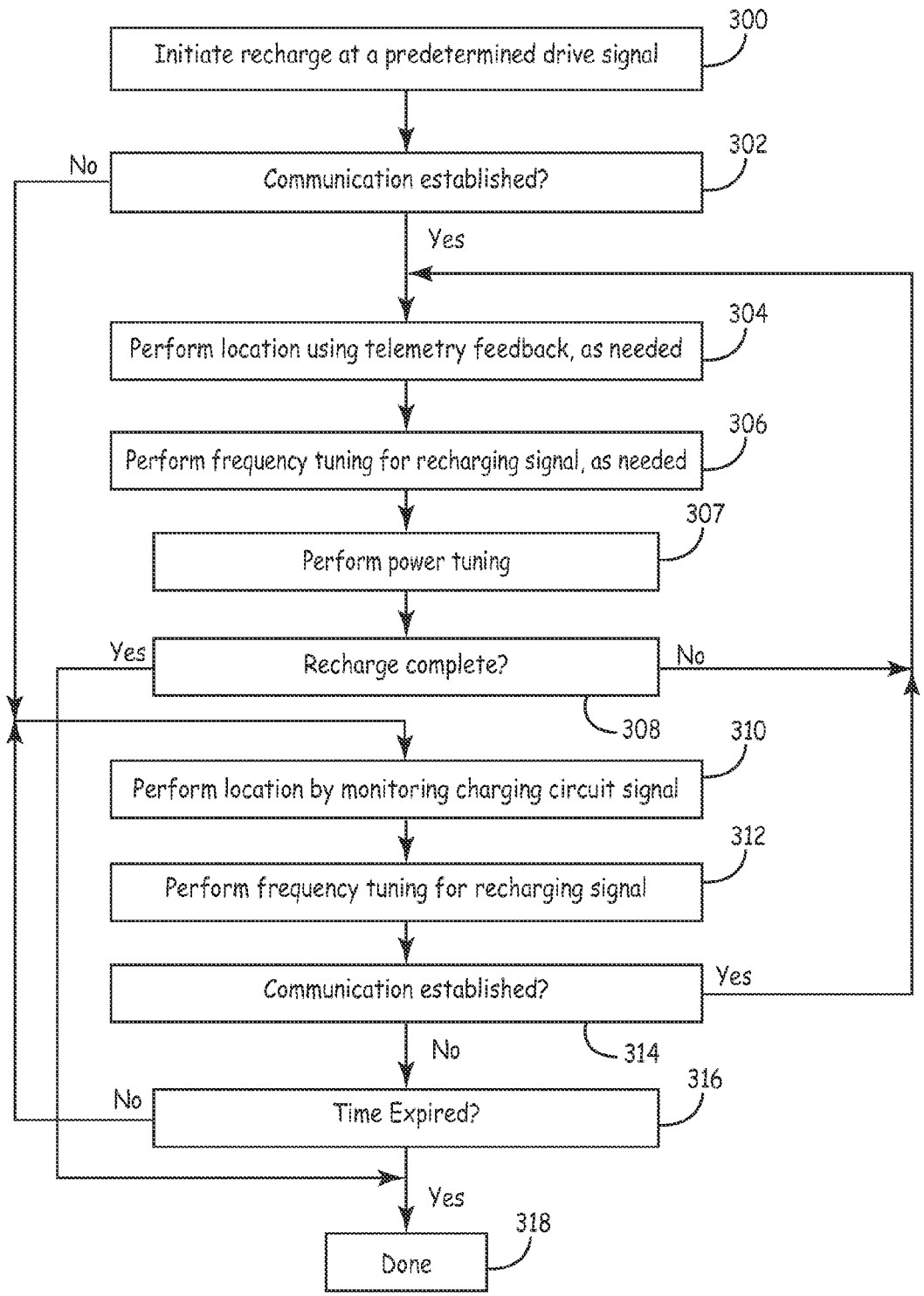
FIG. 11 is a flow diagram illustrating one method of conducting a recharge session according to the current disclosure.

FIG. 11 is a flow diagram illustrating one method of conducting a recharge session according to the current disclosure. Recharge may be initiated using a predetermined drive signal (300). In one instance, this drive signal involves a predetermined voltage level, duty cycle, and frequency. It may be determined whether communication may be established with the IMD (302). If so, locating of the antenna 78 may be performed using telemetry feedback as a guide (304). For instance, IMD 2 may communicate data related to voltage, current and/or magnetic field signals within IMD. As one specific example, IMD 2 may report the amplitude of a current being provided to rechargeable power source 50. This information may be used to gauge recharge coupling quality and determine the optimal recharge location for antenna 78.

The location process of step 304 may be initiated in response to some user input. For instance, a user may depress a button, select a function, use a voice-activated command, or provide some other user input to activate a locating function of charging circuit 70. In another embodiment, the locating function is initiated automatically any time the user initiates a recharge session.

Once the optimal location is determined, frequency tuning may be conducted to determine an optimal frequency for conducting recharge (306). This may be performed using the methods of FIG. 6A or 6B, or any of the many variations that are available as may be appreciated by those skilled in the art and/or as described herein. Of course, in one example, this step may be omitted and a previously-determined value for f(final) may be used for the drive frequency with no further tuning being performed.

Next, tuning of the power level may be performed, if desired (307). Such tuning may be performed in one embodiment using a method such as described in reference to FIG. 10. This tuning may involve altering a voltage and/or a duty cycle at which the H-bridge circuit is being generated.

It may periodically be determined if recharge has completed (308). This may be determined using telemetry feedback from IMD 2. Such feedback may provide a level of the recharge current being provided to rechargeable power source 50, a voltage level of rechargeable power source 50, some combination thereof, or some other signal indicative of a state of charge of rechargeable power source 50.

If it is determined based on feedback that rechargeable power source 50 has been fully, or nearly fully, recharged, the process may be considered complete (318). Otherwise, charging circuit 70 may simply continue recharging while monitoring feedback until IMD 2 reports rechargeable power source 50 is fully, or nearly-fully charged. Of course, a user is free to terminate recharge before this occurs, if desired.

In one example, while conducting recharge, one or more of steps 306-308 may be repeated periodically, as necessary. For instance, if a patient moves antenna 78 inadvertently, it may be necessary to re-locate an antenna position for conducting an adequate recharge session. Such a condition may be determined by a change in a signal being monitored by IMD 2 (e.g., a sudden drop in recharge current into rechargeable power source 50), a change in a signal being monitored by charging circuit (e.g., current in tank circuit 165) or an appearance of stub pulses being detected by edge detect circuit 160. This condition may be reported to the user so that the user may repeat the location steps to re-position antenna 78.

Similarly, if the patient changes posture, flexes antenna 78, or does something else to cause the coupling quality to change, the optimal drive signal and power level for driving the H-bridge circuit may change. Again, this may be detected using any of the techniques discussed above, including by use of a signal monitored by IMD or charging circuit 70, including the appearance of stub pulses as detected by edge detect circuit 160. This change in optimal drive frequency may require that another search be initiated to determine the new optimal frequency and/or duty cycle for driving H-bridge circuit 148. Moreover, a new power level in primary coil 76 may be required to ensure appropriate heat dissipation levels are maintained at, or near, target levels, as shown in step 307.

As may be appreciated, it may be difficult to determine whether loss of antenna location or some other factor (e.g., flexing of antenna or change of patient position) causes a change in a monitored signal (e.g., appearance of stub pulse, etc.) Thus, when such a change occurs, it may be desirable to repeat some, or all, of steps 304-306. As discussed above, if desired, some or all of these steps may be performed at regular intervals, such as once per minute.

Returning to step 302, if communication cannot be established with IMD 2, feedback from the IMD will not be available for locating antenna 78. In this case, a location mechanism that utilizes a signal of charging circuit 70 may be used to perform antenna location (310). For instance, as previously discussed, a voltage-based approach or a frequency-based approach may be used to position antenna. If desired, some combination of these two processes may be employed for this purpose. As discussed above, this location process may be initiated by user interaction, (e.g., a button press, interaction with a touch screen, etc.) Alternatively, this process may be initiated automatically whenever recharge is initiated and communication can not be established with IMD 2.

Once antenna has been positioned, an optimal frequency for performing recharge may be determined in any of the aforementioned ways (312). If a voltage-monitoring approach is being used to locate antenna 78 to conduct recharge as set forth in regards to FIG. 9, the final voltage established during the location process may be used as the voltage at which to tune frequency. Alternatively, voltage may be adjusted somewhat prior to, or after, the frequency tuning process as may be required to reduce heat dissipation.

Periodically, it may be determined whether communication has been established with IMD 2, as may occur when enough charge is provided to rechargeable power source 50 that telemetry module 59 becomes operational (314). If communication has been established, processing may optionally proceed to step 304 to perform re-location of antenna 78 or perform retuning of frequency or power levels. In another embodiment, processing may instead proceed directly to step 308 to determine whether recharge is complete. In either case, once communication is established, recharge may be completed in the manner discussed above with respect to steps 304-308.

In some cases, communication may never be established, as may occur if adequate charge is not being delivered to rechargeable power source 50 because of low coupling quality or some other issue associated with the system. In this case, an expiration time limit may be placed on the recharge session (316). For instance, the session may be conducted for a maximum of ten minutes without communication. If this time limit is reached without establishing communication, the recharge session may terminate (318) and the process is considered complete. In this case, the user may be provided with some guidance on how to proceed next. For instance, user interface 108 of external device 100 and/or a user interface of recharge module 110 may suggest seeking technical assistance. In some examples, confidence tests may be available for execution by a user or technical personnel to verify proper system operation. Alternatively, the user may be provided with guidance on proper recharge techniques and advised to "try again".

As may be appreciated, the methods described herein include many variations. For instance, in many cases, steps of the various methods may be re-ordered without altering the effects and outcomes of the disclosed methods. Moreover, in many cases, the various techniques can be practiced together or separately. For instance, although using a location method in conjunction with frequency tuning may yield optimal recharge results, there is no requirement that frequency tuning be used in conjunction with a location method. Locating antenna 78 may be used alone to determine an antenna position for conducting recharge. Thereafter, some predetermined frequency may be used to perform recharge (e.g., a predetermined recorded value for f(final). Alternatively, a user skilled at positioning antenna 78 in an appropriate recharge location may not need to undergo a location process during each recharge session. Instead that user may proceed directly to frequency tuning, or may even omit this step and use a previously determined value for recharge frequency (e.g., f(final) or another value determined using a variation of frequency tuning.)

Similarly, power tuning need not occur during recharge. For instance, if a power level is selected that is known to be low enough to prevent heat dissipation from exceeding limits, there may be no need to tune power levels. However, in such cases, power levels may be below optimal levels such that recharge will take longer to complete. Conversely, the tuning of power may be performed without use of frequency tuning and/or location methods. Thus, one skilled in the art will appreciate that many variations of the disclosed systems and methods are possible.

It will be appreciated that many embodiments are contemplated by the current disclosure. For instance, whereas the current disclosure describes an embodiment of an H-bridge circuit for generating a signal in tank circuit 165, many other types and configurations of drive circuits are available for this purpose. For instance, a signal generator (e.g. a sine wave generator) may be used for this purpose. The specific embodiments described are to be considered exemplary only and not limiting and the present disclosure is limited only by the claims that follow.

What is claimed is:

1. A charging system configured to transcutaneously deliver power, comprising:
   a primary coil;
   a drive circuit configured to drive the primary coil at a drive frequency; and
   a control circuit configured to tune the drive frequency based on a characteristic of a signal that occurs within the primary coil wherein the signal has a signal level that varies with respect to time, wherein the characteristic is not present when the primary coil is being driven at a resonant frequency of the system and wherein the characteristic comprises at least one transition in the signal level of the signal.

2. The charging system of claim 1, further comprising an edge detect circuit configured to detect the characteristic.

3. The charging system of claim 1, wherein the control circuit is configured to change the drive frequency based on relative timing between the characteristic and another characteristic of the signal.

4. The charging system of claim 1, wherein the characteristic comprises a stub pulse, and wherein the control circuit is configured to decrease the drive frequency if the stub pulse appears within a predetermined time period of another characteristic of the signal and otherwise the control circuit is configured to increase the frequency of the signal.

5. The charging system of claim 1, wherein the drive circuit comprises an H-bridge circuit.

6. The charging system of claim 1, wherein the control circuit is configured to increase a duty cycle at which the primary coil is being driven until the characteristic first appears in the signal at a first frequency, to adjust the drive frequency until the characteristic disappears and reappears at a second frequency, and to adjust the drive frequency to be the average of the first and the second frequencies.

7. The charging system of claim 1, wherein the control circuit is configured to monitor the characteristic of the signal to determine a location at which to position the primary coil to transcutaneously deliver power.

8. The charging system of claim 1, further comprising a detection circuit to detect the characteristic, the detection circuit being coupled to a circuit node associated with the primary coil that is not being driven at a time when the characteristic occurs.

9. The system of claim 1, further comprising:
   a cable coupled to the primary coil; and
   wherein the control circuit is carried by the cable.

10. The system of claim 1, further comprising:
an implantable medical device (IMD) configured to receive the transcutaneously-delivered power; and
a programmer configured to exchange at least one of data and programmed instructions with the IMD, and wherein the programmer comprises, or is communicatively coupled to, the control circuit.

11. The charging system of claim 1, further comprising a tank circuit comprising the primary coil, and wherein the signal is a signal detected in the tank circuit.

12. A charging system configured to transcutaneously deliver power, comprising:
a primary coil;
a drive circuit configured to drive the primary coil at a drive frequency; and
a control circuit configured to tune the drive frequency based on a characteristic of a signal that is associated with the primary coil, wherein the characteristic is not present when the primary coil is being driven at a resonant frequency of the system, wherein the characteristic comprises a stub pulse, and wherein the control circuit is configured to change the drive frequency by an amount that is based on a width of the stub pulse.

13. A charging system configured to transcutaneously deliver power, comprising:
a primary coil;
a drive circuit configured to drive the primary coil at a drive frequency; and
a control circuit configured to tune the drive frequency based on a characteristic of a signal that is associated with the primary coil, wherein the characteristic is not present when the primary coil is being driven at a resonant frequency of the system and wherein the control circuit is configured to determine a high frequency at which the characteristic first appears in the signal and a low frequency at which the characteristic first appears in the signal, and to adjust the drive frequency to be the average of the high and the low frequencies.

14. A charging system configured to transcutaneously deliver power, comprising:
a primary coil;
a drive circuit configured to drive the primary coil at a drive frequency; and
a control circuit configured to tune the drive frequency based on a characteristic of a signal that is associated with the primary coil, wherein the characteristic is not present when the primary coil is being driven at a resonant frequency of the system and wherein the control circuit is configured to adjust the drive frequency until the characteristic disappears at a first frequency and reappears at a second frequency, and to adjust the drive frequency to be the average of the first and second frequencies.

15. A charging system configured to transcutaneously deliver power, comprising:
a primary coil;
a drive circuit configured to drive the primary coil at a drive frequency; and
a control circuit configured to tune the drive frequency based on a characteristic of a signal that is associated with the primary coil, wherein the characteristic is not present when the primary coil is being driven at a resonant frequency of the system, wherein the drive circuit is configured to enforce a dead period during which the primary coil is not being driven and wherein the characteristic occurs during the dead period.

16. A system, comprising:
a circuit configured to generate a signal associated with transcutaneously delivering power, and to tune the signal to a resonant frequency of the system based on a characteristic in the signal that is not present when the signal is at the resonant frequency of the system, wherein the characteristic comprises a negative-to-positive-going or a positive-to-negative-going transition.

17. The system of claim 16, wherein the circuit is configured to adjust the frequency of the signal based on relative timing between the characteristic in the signal that is not present when the signal is at the resonant frequency of the system and a characteristic of the signal that is present when the signal is at the resonant frequency of the system.

18. The system of claim 17, wherein the negative-to-positive-going or the positive-to-negative-going transition comprises multiple different amplitude levels.

19. The system of claim 16, wherein the characteristic in the signal that is not present when the signal is at the resonant frequency of the system comprises a stub pulse.

20. The system of claim 16, wherein the circuit is configured to automatically tune the signal based on a predetermined trigger event occurring while transcutaneously delivering power.

21. The system of claim 16, further comprising an implantable medical device to receive the transcutaneously delivered power.

22. A method of transcutaneously delivering power, comprising:
driving a primary coil;
monitoring a signal that occurs within the primary coil;
detecting a transition in the monitored signal, the transition occurring with respect to time; and
adjusting a drive signal that is driving the primary coil to a resonant frequency based on a characteristic in the monitored signal that is not present when the drive signal is at the resonant frequency, wherein the characteristic comprises the detected transition.

23. The method of claim 22, further comprising adjusting a location of the primary coil by monitoring at least one of a frequency at which the primary coil is being driven or a voltage at which the primary coil is being driven.

24. The method of claim 22, wherein detecting a transition in the monitored signal comprises detecting multiple amplitude levels in the monitored signal.

25. The method claim 22, wherein adjusting the drive signal comprises adjusting a frequency of the drive signal based on relative timing of the characteristic in the monitored signal that is not present when the drive signal is at the resonant frequency and a characteristic of the monitored signal that is present when the drive signal is at the resonant frequency.

26. The method of claim 22, wherein the characteristic comprises a pulse, and further comprising adjusting the frequency of the drive signal by an amount that is based on a width of the pulse.

27. The method of claim 22, further comprising:
adjusting the frequency of the drive signal until the characteristic appears at a high frequency;
adjusting the frequency of the drive signal until the characteristic appears at a low frequency; and
setting the frequency of the drive signal to the average of the high and low frequencies.

28. The method of claim 22, further comprising monitoring a signal to determine a physical location at which to position the primary coil while the primary coil is being driven.

29. The method of claim 28, wherein the signal monitored to determine the physical location is the monitored signal that occurs within the primary coil.

30. The system of claim 16, wherein the circuit comprises a tank circuit and the signal appears in the tank circuit.

31. A system, comprising:
coil means for transcutaneously delivering power;
signal generation means for generating a signal that causes a waveform to occur in the coil means; and
control means for tuning a frequency of the signal based on a characteristic of the waveform that varies with respect to time and that is not present when the coil means is driven at a resonant frequency of the system.

32. The system of claim 31, further comprising implantable medical device means for receiving the transcutaneously delivered power.

* * * * *